(12) United States Patent
Musa et al.

(10) Patent No.: US 10,905,636 B2
(45) Date of Patent: Feb. 2, 2021

(54) BLOCK COPOLYMERS COMPRISING REPEATING UNITS DERIVED FROM MONOMERS COMPRISING LACTAM AND ACRYLOYL MOIETIES AND HYDROPHOBIC MONOMERS, COMPOSITIONS, AND APPLICATIONS THEREOF

(71) Applicant: ISP INVESTMENTS LLC, Wilmington, DE (US)

(72) Inventors: Osama M. Musa, Bedminster, NJ (US); Victoria Jane Cunningham, Yorkshire (GB); Steven Peter Armes, Yorkshire (GB)

(73) Assignee: ISP INVESTMENTS LLC, Wilmington, DE (US)

( * ) Notice: Subject to any disclaimer, the term of this patent is extended or adjusted under 35 U.S.C. 154(b) by 153 days.

(21) Appl. No.: 16/069,770

(22) PCT Filed: Jan. 11, 2017

(86) PCT No.: PCT/US2017/012915
§ 371 (c)(1),
(2) Date: Jul. 12, 2018

(87) PCT Pub. No.: WO2017/123572
PCT Pub. Date: Jul. 20, 2017

(65) Prior Publication Data
US 2019/0015304 A1    Jan. 17, 2019

Related U.S. Application Data

(60) Provisional application No. 62/277,240, filed on Jan. 11, 2016.

(51) Int. Cl.

| | | |
|---|---|---|
| *C08F 293/00* | (2006.01) | |
| *A61K 8/06* | (2006.01) | |
| *A61K 8/81* | (2006.01) | |
| *C08L 35/02* | (2006.01) | |
| *C08F 220/18* | (2006.01) | |
| *C08F 220/34* | (2006.01) | |
| *C08F 220/60* | (2006.01) | |
| *C08F 222/22* | (2006.01) | |
| *C08F 222/38* | (2006.01) | |

(52) U.S. Cl.
CPC .............. *A61K 8/06* (2013.01); *A61K 8/8152* (2013.01); *A61K 8/8158* (2013.01); *C08F 293/005* (2013.01); *C08L 35/02* (2013.01); *C08F 220/18* (2013.01); *C08F 220/1818* (2020.02); *C08F 220/34* (2013.01); *C08F 220/60* (2013.01); *C08F 222/22* (2013.01); *C08F 222/38* (2013.01); *C08F 2438/03* (2013.01)

(58) Field of Classification Search
CPC .. C08F 293/005; C08F 220/34; C08F 220/60; C08F 222/22; C08F 222/38; C08F 2220/1891; C08F 2438/03; C08F 293/00
See application file for complete search history.

(56) References Cited

U.S. PATENT DOCUMENTS

| | | |
|---|---|---|
| 5,461,125 A | 10/1995 | Lu et al. |
| 6,465,588 B1 | 10/2002 | Li |
| 2005/0238594 A1* | 10/2005 | Mougin ................ A61K 8/046 424/59 |
| 2006/0039934 A1 | 2/2006 | Ness et al. |

OTHER PUBLICATIONS

Jia, S. et al. Sensors and Actuators B: Chemical vol. 138 pp. 244-250 (Year: 2009).*
Shi, Y. et al. ACS Macro Letters vol. 3 pp. 70-73 (Year: 2013).*
Search Report of PCT Application No. PCT/US17/012915 Publication Under No. WO2017123572 dated Jul. 20, 2017.

* cited by examiner

*Primary Examiner* — Irina S Zemel
*Assistant Examiner* — Jeffrey S Lenihan
(74) *Attorney, Agent, or Firm* — William J. Davis; Nathalie Tietcheu

(57) ABSTRACT

The invention provides block copolymers comprising at least one block A comprising repeating units derived from monomers comprising lactam and acryloyl moieties and at least one block B comprising repeating units derived from hydrophobic monomers. The invention further provides compositions comprising the block copolymers and applications thereof in various industrial areas including personal care. The invention furthermore provides compositions comprising colloidal particles of the block copolymers. The variables x, y, $R_8$ and $R_9$ are described herein.

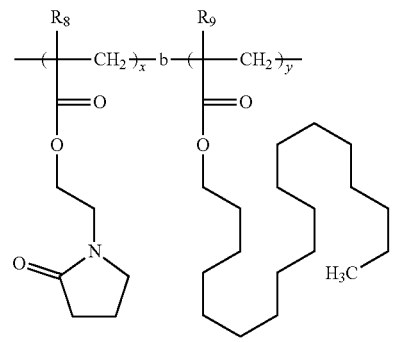

1 Claim, No Drawings

BLOCK COPOLYMERS COMPRISING REPEATING UNITS DERIVED FROM MONOMERS COMPRISING LACTAM AND ACRYLOYL MOIETIES AND HYDROPHOBIC MONOMERS, COMPOSITIONS, AND APPLICATIONS THEREOF

BACKGROUND

Field of the Invention

The disclosed and/or claimed inventive concept(s) provides block copolymers comprising at least one block consisting of repeating units derived from monomers comprising lactam and acryloyl moieties and at least one block comprising repeating units derived from hydrophobic monomers. The disclosed and/or claimed inventive concept(s) further provides compositions comprising the block copolymers and applications thereof in various industrial areas including personal care.

Description of Related Art

It is well-known that AB type of diblock copolymers undergo self-assembly both in the solid state and also in solution. In the latter case, a diverse range of copolymer morphologies has been reported, including spheres, worms, or vesicles. Typically, the copolymer chains are first prepared in a non-selective solvent and then subjected to either a gradual change in solvency or a pH switch in a separate step, which is typically undertaken in dilute solution.

In recent years, polymerization-induced self-assembly (PISA) of diblock copolymers in a solvent that is selective for the growing second block has become increasingly popular. PISA offers two decisive advantages over traditional processing methods: (i) syntheses can be conducted at up to 50% w/w solids and (ii) diblock copolymer nanoparticles are obtained directly, without requiring any post-polymerization processing steps. When combined with PISA, controlled radical polymerization techniques such as atom transfer radical polymerization (ATRP) or reversible addition-fragmentation chain transfer (RAFT) polymerization have enabled the preparation of a wide range of well-defined nanoparticles. RAFT dispersion polymerization is known to allow the efficient synthesis of pure spherical, worm-like or vesicular morphologies in aqueous, alcoholic, or non-polar media as well as ionic liquids.

Synthesis and self-assembly behaviors of well-defined poly(lauryl methacrylate)-block-poly [N-(2-methacryloylxyethyl)pyrrolidone] copolymers is described by Zhang and coworkers in *Colloid and Polymer Science*, 2013, volume 291, 2653-2662.

Direct electrochemistry and electrocatalysis of hemoglobin immobilized in an amphiphilic diblock copolymer film is described by Jia and coworkers in *Sensors & Actuators: B. Chemical*, 2009, volume 138, 244-250.

Facile synthesis and thermoresponsive behavior of a well-defined pyrrolidone based hydrophilic polymer is described by Deng and coworkers in *Macromolecules*, 2008, volume 41, 3007-3014.

Effect of mild visible light on rapid aqueous RAFT polymerization of water-soluble acrylic monomers at ambient temperature: initiation and activation is described by Cai and coworkers in *Macromolecules*, 2009, volume 42, 3917-3926.

Pyrrolidone-functional smart polymers via nitroxide-mediated polymerization is described by Savelyeva and coworkers in *J Poly Sci. Part A Polymer Chem.*, 2014, volume 52, issue 14, 2011-2024.

Effect of molecular structure on thermoresponsive behaviors of pyrrolidone-based water-soluble polymers is described by Cai and coworkers in *Macromolecules*, 2010, volume 43, 4041-4049.

U.S. published Pat. App. 2005/0238594 discloses ethylenic copolymers comprising a vinyllactam block, cosmetic or pharmaceutical compositions comprising them and cosmetic use of these copolymers.

It has been found that block copolymers and compositions according to the disclosed and/or claimed inventive concept(s) have unique and important performance attributes due to which they can be advantageously used in various industrial applications including personal care. Non-limiting examples of personal care applications include sun care compositions, face care compositions, lip care compositions, eye care compositions, skin care compositions, after-sun compositions, body care compositions, nail care compositions, anti-aging compositions, insect repellants, oral care compositions, deodorant compositions, hair care compositions, conditioning compositions, color cosmetic compositions, color-protection compositions, self-tanning compositions, and foot care compositions.

SUMMARY

In a first aspect, the disclosed and/or claimed inventive concept(s) provides a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

In a second aspect, the disclosed and/or claimed inventive concept(s) provides a composition comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate. Non-limiting examples of the compositions include personal care compositions, coating compositions, construction compositions, oilfield compositions, drilling fluids, drilling muds, cementing fluids, servicing fluids, gravel packing muds, fracturing fluids, completion fluids, workover fluids, spacer fluids, household, industrial and institutional compositions, pharmaceutical compositions, food compositions, biocides, adhesives, inks, papers, polishes, membranes, metal working fluids, plastics, textiles, printing compositions, lubricants, preservatives, agrochemicals, and wood-care compositions. In one non-limiting embodiment, the composition is a personal care composition.

In a third aspect, the disclosed and/or claimed inventive concept(s) provides a personal care composition comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

In a fourth aspect, the disclosed and/or claimed inventive concept(s) provides a composition in the form of colloidal particles comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

In a fifth aspect, the disclosed and/or claimed inventive concept(s) provides a Pickering emulsion composition comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

DETAILED DESCRIPTION

Before explaining at least one aspect of the disclosed and/or claimed inventive concept(s) in detail, it is to be understood that the disclosed and/or claimed inventive concept(s) is not limited in its application to the details of construction and the arrangement of the components or steps or methodologies set forth in the following description or illustrated in the drawings. The disclosed and/or claimed inventive concept(s) is capable of other aspects or of being practiced or carried out in various ways. Also, it is to be understood that the phraseology and terminology employed herein is for the purpose of description and should not be regarded as limiting.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications referenced in any portion of this application are herein expressly incorporated by reference herein their entirety to the same extent as if each individual patent or publication was specifically and individually indicated to be incorporated by reference.

All of the articles and/or methods disclosed herein can be made and executed without undue experimentation in light of the present disclosure. While the articles and methods of the disclosed and/or claimed inventive concept(s) have been described in terms of aspects, it will be apparent to those of ordinary skill in the art that variations may be applied to the articles and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

As utilized in accordance with the disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, $B_{Xn}$, $B_{Xn+1}$, or combinations thereof" is intended to include at least one of: A, $B_{Xn}$, $B_{Xn+1}$, $AB_{Xn}$, A $B_{Xn+1}$, $B_{Xn}B_{Xn+1}$, or $AB_{Xn}B_{Xn+1}$ and, if order is important in a particular context, also $B_{Xn}A$, $B_{Xn+1}A$, $B_{Xn+1}B_{Xn}$, $B_{Xn+1}B_{Xn}A$, $B_{Xn}B_{Xn+1}A$, $AB_{Xn+1}B_{Xn}$, $B_{Xn}AB_{Xn+1}$, or $B_{Xn+1}AB_{Xn}$. Continuing with this example, expressly included are combinations that contain repeats of one or more item or term, such as $B_{Xn}B_{Xn}$, AAA, $MB_{Xn}$, $B_{Xn}B_{Xn}B_{Xn+1}$, $AAAB_{Xn}B_{Xn+1}B_{Xn+1}B_{Xn+1}$, $B_{Xn+1}B_{Xn}B_{Xn}AAA$, $B_{Xn+1}A$ $B_{Xn}AB_{Xn}B_{Xn}$, and so forth. The skilled artisan will understand that typically there is no limit on the number of items or terms in any combination, unless otherwise apparent from the context.

The term "each independently selected from the group consisting of" means when a group appears more than once in a structure, that group may be selected independently each time it appears.

The term "hydrocarbyl" includes straight-chain and branched-chain alkyl, alkenyl, alkynyl, cycloalkyl, cycloalkenyl, aryl groups, and combinations thereof with optional heteroatom(s). A hydrocarbyl group may be mono-, di- or polyvalent.

The term "alkyl" refers to a functionalized or unfunctionalized, monovalent, straight-chain, branched-chain, or cyclic $C_1$-$C_{60}$ hydrocarbyl group optionally having one or more heteroatoms. In one non-limiting embodiment, an alkyl is a $C_1$-$C_{45}$ hydrocarbyl group. In another non-limiting embodiment, an alkyl is a $C_{1-C30}$ hydrocarbyl group. Non-limiting examples of alkyl include methyl, ethyl, n-propyl, isopropyl, n-butyl, isobutyl, tert-butyl, n-pentyl, isopentyl, n-hexyl, n-heptyl, n-octyl, 2-ethylhexyl, tert-octyl, iso-norbornyl, n-dodecyl, tert-dodecyl, n-tetradecyl, n-hexadecyl, n-octadecyl, n-eicosyl, cyclobutyl, cyclopentyl, cyclohexyl, and the like. The definition of "alkyl" also includes groups obtained by combinations of straight-chain, branched-chain and/or cyclic structures.

The term "aryl" refers to a functionalized or unfunctionalized, monovalent, aromatic hydrocarbyl group optionally having one or more heteroatoms. The definition of aryl includes carbocyclic and heterocyclic aromatic groups. Non-limiting examples of aryl groups include phenyl, naphthyl, indenyl, indanyl, azulenyl, fluorenyl, anthracenyl, furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl, and the like.

The term "aralkyl" refers to an alkyl group comprising one or more aryl substituent(s) wherein "aryl" and "alkyl" are as defined above. Non-limiting examples of aralkyl groups include benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "alkylene" refers to a functionalized or unfunctionalized, divalent, straight-chain, branched-chain, or cyclic $C_1$-$C_{40}$ hydrocarbyl group optionally having one or more heteroatoms. In one non-limiting embodiment, an alkylene is a $C_1$-$C_{30}$ group. In another non-limiting embodiment, an alkylene is a $C_1$-$C_{20}$ group. Non-limiting examples of alkylene groups include:

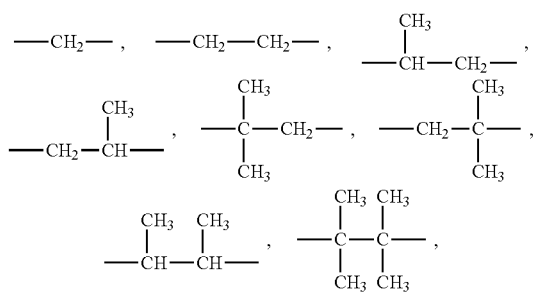

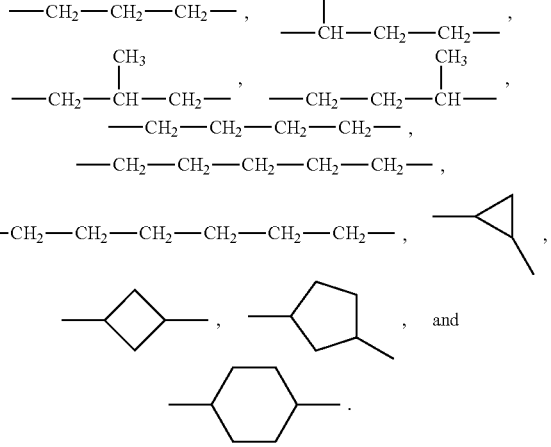

The term "arylene" refers to a functionalized or unfunctionalized, divalent, aromatic hydrocarbyl group optionally having one or more heteroatoms. The definition of arylene includes carbocyclic and heterocyclic groups. Non-limiting examples of arylene groups include phenylene, naphthylene, pyridinylene, and the like.

The term "heteroatom" refers to oxygen, nitrogen, sulfur, silicon, phosphorous, or halogen. The heteroatom(s) may be present as a part of one or more heteroatom-containing functional groups. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups. The heteroatom(s) may also be present as a part of a ring such as in heteroaryl and heteroarylene groups.

The term "halogen" or "halo" refers to Cl, Br, I, or F.

The term "ammonium" includes protonated $NH_3$ and protonated primary, secondary, and tertiary organic amines.

The term "functionalized" with reference to any moiety refers to the presence of one or more functional groups in the moiety. Various functional groups may be introduced in a moiety by way of one or more functionalization reactions known to a person having ordinary skill in the art. Non-limiting examples of functionalization reactions include: alkylation, epoxidation, sulfonation, hydrolysis, amidation, esterification, hydroxylation, dihydroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. In one non-limiting embodiment, the term "functionalized" with reference to any moiety refers to the presence of one more functional groups selected from the group consisting of alkyl, alkenyl, hydroxyl, carboxyl, halogen, alkoxy, amino, imino, and combinations thereof, in the moiety.

The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many.

Non-limiting examples of polymers include homopolymers, and non-homopolymers such as copolymers, terpolymers, tetrapolymers and the higher analogues. The polymer may have a random, block, and/or alternating architecture.

The term "homopolymer" refers to a polymer that consists essentially of a single monomer type.

The term "non-homopolymer" refers to a polymer that comprises more than one monomer types.

The term "copolymer" refers to a non-homopolymer that comprises two different monomer types.

The term "terpolymer" refers to a non-homopolymer that comprises three different monomer types.

The term "branched" refers to any non-linear molecular structure. The term includes both branched and hyper-branched structures.

The term "block copolymer" refers to a polymer comprising at least two blocks of polymerized monomers. Any block may be derived from either a single monomer resulting in a homopolymeric subunit, or two or more monomers resulting in a copolymeric (or non-homopolymeric) subunit in the block copolymer. The block copolymers may be diblock copolymers (i.e., polymers comprising two blocks of monomers), triblock copolymers (i.e., polymers comprising three blocks of monomers), multiblock copolymers (i.e., polymers comprising more than three blocks of monomers), and combinations thereof. The block copolymers may be linear, branched, star or comb like, and have structures such as [A][B], [A][B][A], [A][B][C], [A][B][A][B], [A][B][C][B], etc. An exemplary representation of block copolymer is $[A]_x[B]_y$ or $[A]_x[B]_y[C]_z$, wherein x, y and z are the degrees of polymerization (DP) of the corresponding blocks [A], [B], and [C]. Additional insight into the chemistry, characterization and applications of block copolymers may be found in the book '*Block Copolymers: Synthetic Strategies, Physical Properties, and Applications*', by Nikos Hadjichristidis, Stergios Pispas, and George Floudas, John Wiley and Sons (2003), the contents of which are herein incorporated in its entirety by reference.

The term "controlled radical polymerization" refers to a specific radical polymerization process, also denoted by the term of "living radical polymerization", in which use is made of control agents, such that the block copolymer chains being formed are functionalized by end groups capable of being reactivated in the form of free radicals by virtue of reversible transfer or reversible termination reactions.

The term "addition-fragmentation" refers to a two-step chain transfer mechanism during polymerization of block copolymers wherein a radical addition is followed by fragmentation to generate a new radical species.

The term "free radical addition polymerization initiator" refers to a compound used in a catalytic amount to initiate a free radical addition polymerization. The choice of initiator depends mainly upon its solubility and its decomposition temperature.

The term "alkyl acrylate" refers to an alkyl ester of an acrylic acid or an alkyl acrylic acid.

The term "alkyl acrylamide" refers to an alkyl amide of an acrylic acid or an alkyl acrylic acid.

The term "moiety" refers to a part or a functional group of a molecule.

In the block copolymer structures, the notation -b- on the polymer backbone is meant to denote block configuration of repeating units. An exemplary block copolymer structure is shown below:

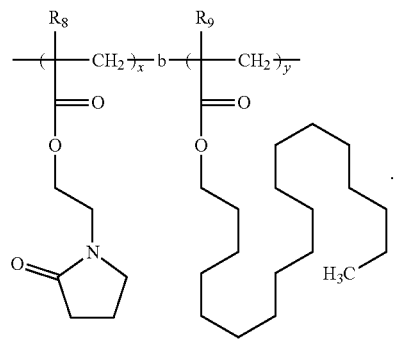

The terms "personal care composition" and "cosmetics" refer to compositions intended for use on or in the human body, such as skin, sun, hair, oral, cosmetic, and preservative compositions, including those to alter the color and appearance of skin and hair.

The term "pharmaceutical composition" refers to any composition comprising at least one pharmaceutically active ingredient, as well as any product which results, directly or indirectly, from combination, complexation, or aggregation of any two or more of the ingredients, from dissociation of one or more of the ingredients, or from other types of reactions or interactions of one or more of the ingredients.

The term "coating composition" refers to an aqueous-based or solvent-based liquid composition that may be applied to a substrate and thereafter solidified (for example, by radiation, air curing, post-crosslinking or ambient temperature drying) to form a hardened coating on the substrate.

The term "Pickering emulsion" refers to an emulsion of any type, either oil-in-water (o/w), water-in-oil (w/o), or multiple emulsion, stabilized by the presence of nanometric or micrometric solid particles at the interface between the different phases.

The term "colloidal" refers to the state of matter having nanometer dimensions.

The term "oilfield composition" refers to a composition that may be used in the exploration, extraction, recovery, and/or completion of any hydrocarbon. Non-limiting examples of oilfield compositions include drilling fluids, cementing fluids, anti-agglomerants, kinetic hydrate inhibitors, shale swelling inhibitors, drilling muds, servicing fluids, gravel packing muds, friction reducers, fracturing fluids, completion fluids, and work over fluids.

The term "hydrophobic monomer" refers to a monomer having solubility in water of less than about 1 percent by weight at 25° C.

All percentages, ratio, and proportions used herein are based on a weight basis unless other specified.

In a first aspect, the disclosed and/or claimed inventive concept(s) provides a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

In one non-limiting embodiment, each monomer $a_1$ and $a_2$ independently has a structure:

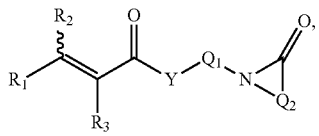 (1)

wherein each $R_1$, $R_2$ and $R_3$ is independently selected from the group consisting of hydrogen, halogens, functionalized and unfunctionalized $C_1$-$C_4$ alkyl, and

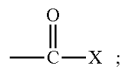

each X is independently selected from the group consisting of $OR_4$, OM, halogen, $N(R_5)(R_6)$,

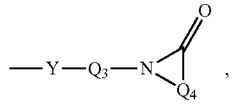

and combinations thereof; each Y is independently oxygen, $NR_7$ or sulfur; each $R_4$, $R_5$, $R_6$ and $R_7$ is independently selected from the group consisting of hydrogen, functionalized and unfunctionalized alkyl, and combinations thereof; each M is independently selected from the group consisting of metal ions, ammonium ions, organic ammonium cations, and combinations thereof; and each $Q_1$, $Q_2$, $Q_3$, and $Q_4$ is independently a functionalized or unfunctionalized alkylene.

In one non-limiting embodiment, each $Q_1$, $Q_2$, $Q_3$, and $Q_4$ is independently selected from the group consisting of functionalized and unfunctionalized $C_1$-$C_{12}$ alkylene. Non-limiting examples of such alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)CH(CH_3)$—, —$C(CH_3)_2$—$C(CH_3)_2$—,
—$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, and —$CH_2$—$CH_2$—$CH_2$—$CH_2$—$CH_2$—$CH_2$—$CH_2$—.

In another non-limiting embodiment, each $Q_1$, $Q_2$, $Q_3$, and Q is independently selected from the group consisting of functionalized and unfunctionalized $C_2$-$C_6$ alkylene. Non-limiting examples of such alkylene groups include:

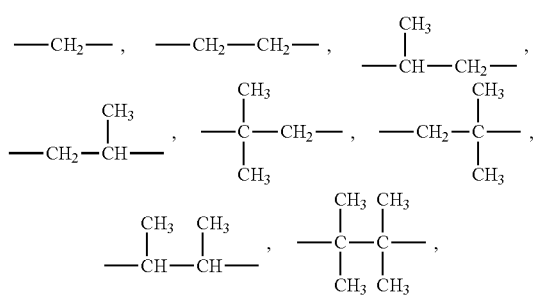

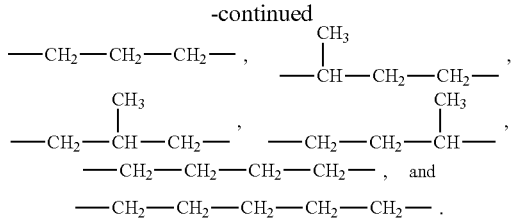

In one non-limiting embodiment, each $R_1$, $R_2$ and $R_3$ is independently selected from the group consisting of hydrogen, methyl and combinations thereof. In another non-limiting embodiment, $R_1$ and $R_2$ are hydrogens and $R_3$ is hydrogen or methyl.

In another non-limiting embodiment, each $R_1$ and $R_3$ is independently hydrogen or methyl; $R_2$ is

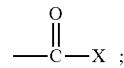

X is selected from the group consisting of $OR_4$, OM, halogens, and $N(R_5)(R_6)$; each $R_4$, $R_5$, and $R_6$ is independently selected from the group consisting of hydrogen and functionalized and unfunctionalized alkyl; and each M is independently selected from the group consisting of metal ions, ammonium ions, organic ammonium cations, and combinations thereof.

In yet another non-limiting embodiment, $R_1$ and $R_3$ are hydrogens and $R_2$ is

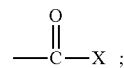

X is selected from the group consisting of $OR_4$, OM and $N(R_5)(R_6)$; each $R_4$, $R_5$, and $R_6$ is independently selected from the group consisting of hydrogen and functionalized and unfunctionalized $C_1$-$C_4$ alkyl; and each M is independently selected from the group consisting of metal ions, ammonium ions, organic ammonium cations, and combinations thereof.

Each monomer $a_1$ and $a_2$ independently maybe be synthesized using methods described in the art, e.g., by reaction of an N-hydroxylalkyl lactam with carboxylic acids such as (meth)acrylic acid, esters such as (meth)acrylate esters, amides such as (meth)acrylamides, anhydrides such as (meth)acrylic anhydride, or similar compounds. Methods of synthesis include those described in patents: U.S. Pat. Nos. 2,882,262; 5,523,340; 6,369,163; U.S. Pat. Application Publication 2007/123673; GB924623; GB930668; GB1404989; WO03/006569; and EP385918. Each of the aforementioned patents is herein incorporated by reference in its entirety.

Non-limiting examples of N-hydroxyalkyl lactams include N-hydroxymethyl pyrrolidone, N-hydroxymethyl caprolactam, N-hydroxyethyl pyrrolidone, N-hydroxyethyl caprolactam, N-hydroxypropyl pyrrolidone, and N-hydroxypropyl caprolactam. Non-limiting examples of carboxylic acids include: acrylic acid, methacrylic acid, itaconic acid, crotonic acid, fumaric acid, succinic acid, and maleic acid. Non-limiting examples of acrylates and (meth)acrylates include methyl, ethyl, butyl, n-octyl, 2-ethylhexyl acrylates and their (meth)acrylate analogues. Non-limiting examples of anhydrides include (meth)acrylic anhydride, formic anhydride, succinic anhydride, and maleic anhydride.
In one non-limiting embodiment, each monomer $a_1$ and $a_2$ has a structure independently selected from the group consisting of:
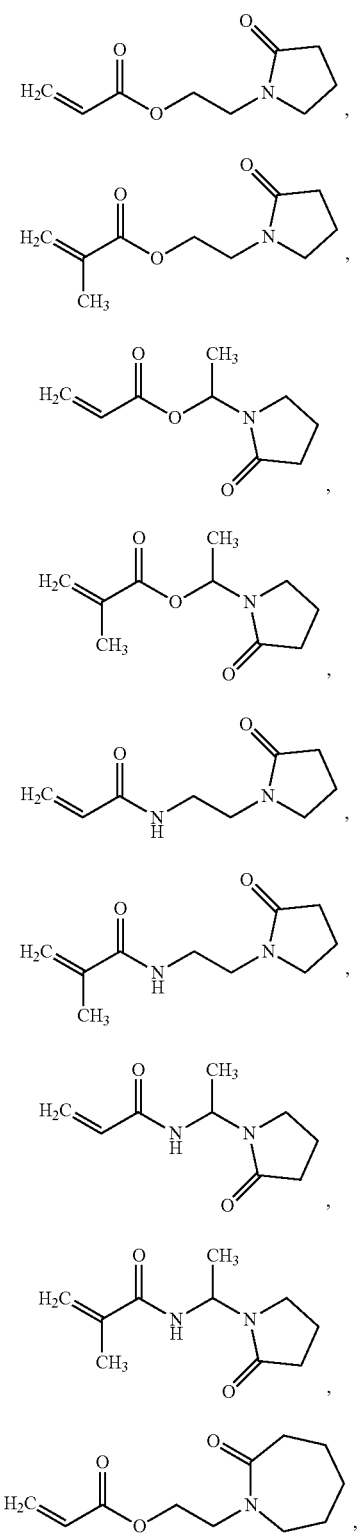
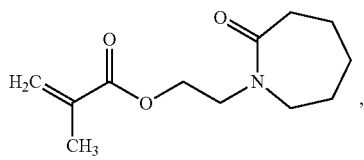
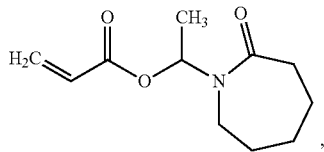
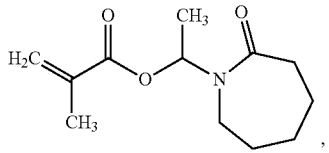
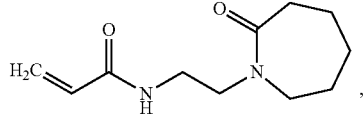
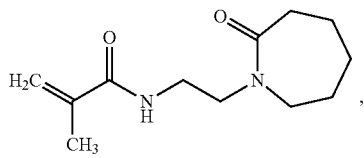
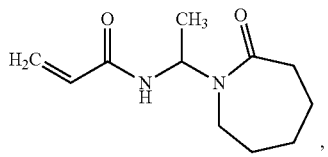
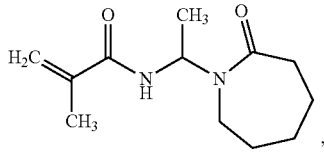
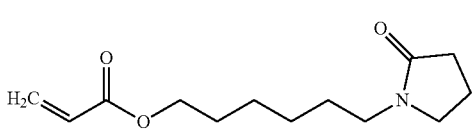
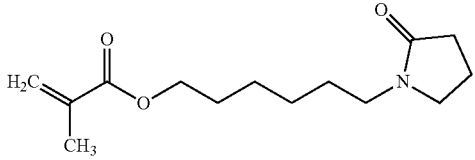
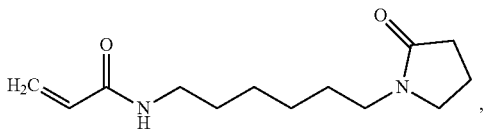

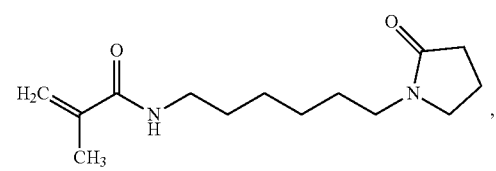(21)
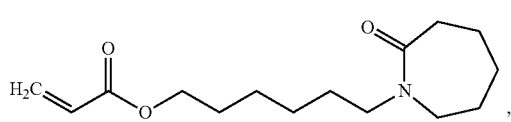(22)
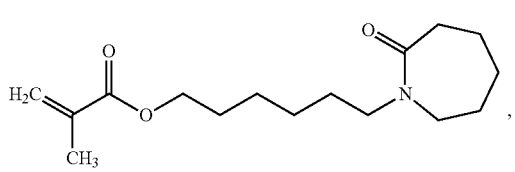(23)
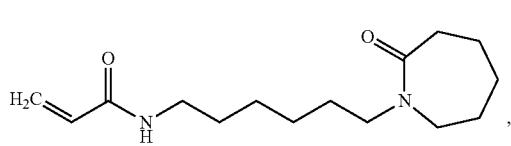(24)
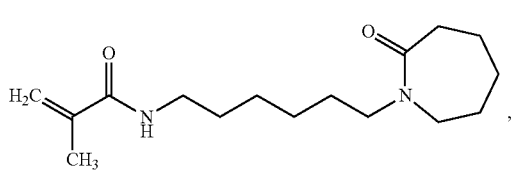(25)
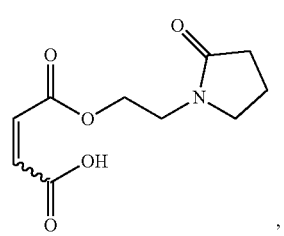(26)
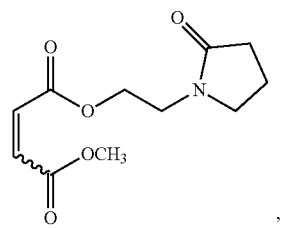(27)
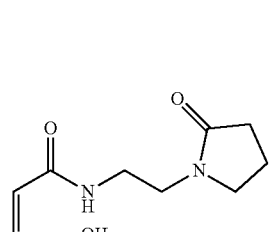(28)
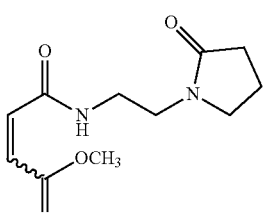(29)
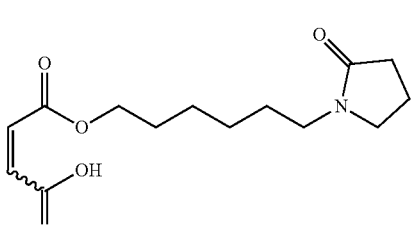(30)
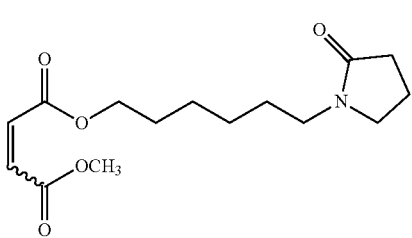(31)
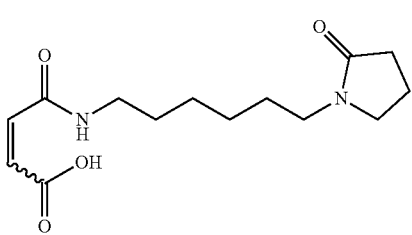(32)
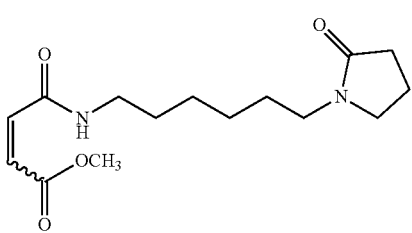(33)
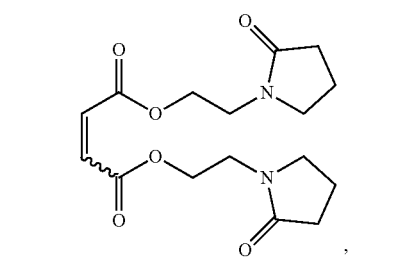(34)

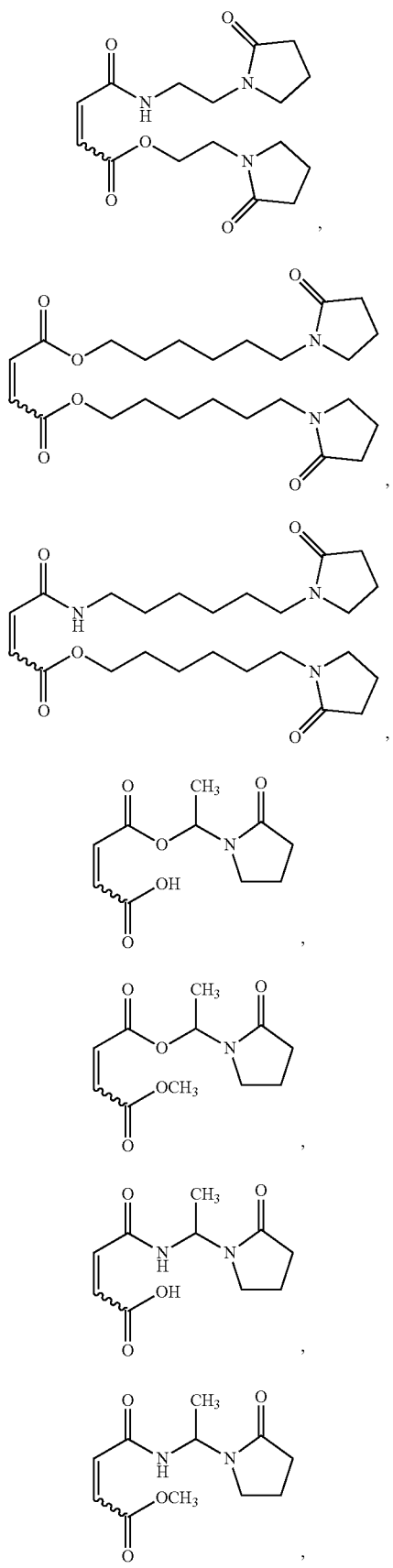
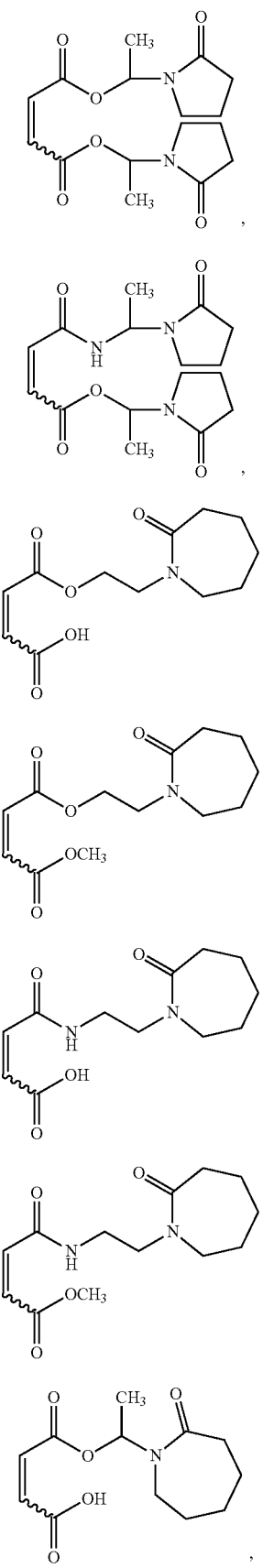

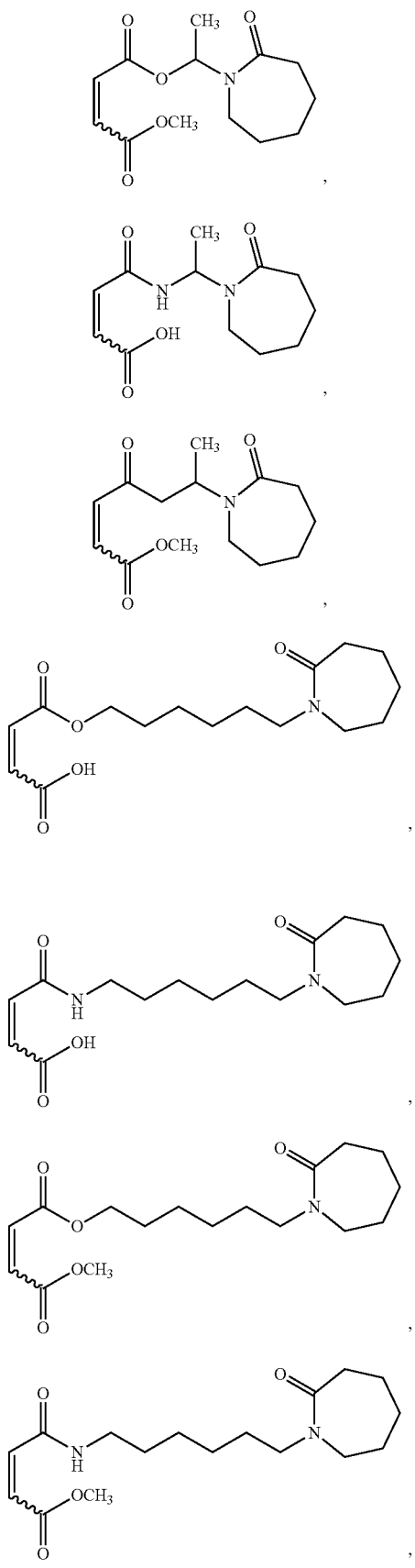

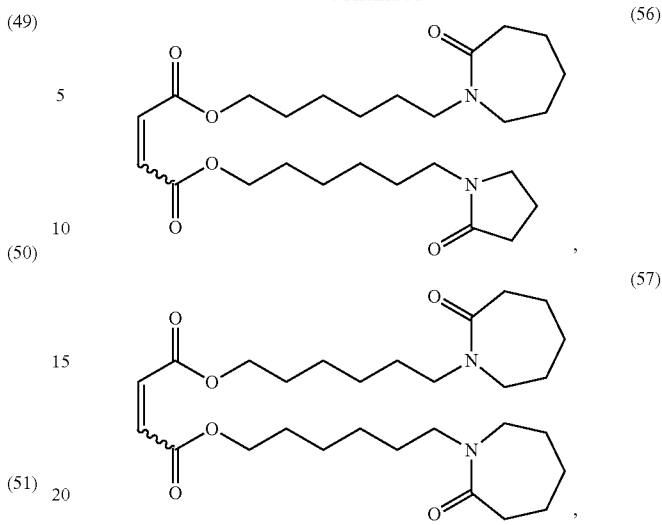

and combinations thereof.

Further non-limiting examples of monomers $a_1$ and $a_2$ can be found in WO2011/063208, the disclosure of which is herein incorporated by reference in its entirety.

In one non-limiting embodiment, the monomer $b_1$ is selected from the group consisting of monomers comprising at least one acryloyl moiety, vinyl lactams, alkyl vinyl ethers, aryl vinyl ethers, vinyl alkanoates, vinyl alkanamides, vinyl alcohols, vinyl carbonates, vinyl carbamates, vinyl thiocarbamates, vinyl ureas, vinyl halides, vinyl imidazoles, vinyl pyridines, vinyl silanes, vinyl siloxanes, vinyl sulfones, alpha, beta-olefinically unsaturated carboxylic anhydrides, diacids, diesters, ester acids, amic acids, diamides, imides, ester amides, alpha-olefins, vinyl triazoles, alpha, beta-olefinically unsaturated carboxylic nitriles, vinyl aromatics, and combinations thereof.

In another non-limiting embodiment, the monomer $b_1$ is selected from the group consisting of monomers comprising at least one acryloyl moiety, vinyl lactams, alkyl vinyl ethers, vinyl alkanoates, alpha, beta-olefinically unsaturated carboxylic nitriles, vinyl aromatics, and combinations thereof.

In one non-limiting embodiment, the monomer comprising at least one acryloyl moiety is selected from the group consisting of functionalized and unfunctionalized $C_{13}$-$C_{40}$ alkyl (meth)acrylic acids and salts thereof, $C_{13}$-$C_{40}$ alkyl (meth)acrylates, $C_{13}$-$C_{40}$ alkyl (meth)acrylamides, aralkyl (meth)acrylic acids and salts thereof, aralkyl (meth)acrylates, aralkyl (meth)acrylamides, and combinations thereof.

In one non-limiting embodiment, the monomer $b_1$ is selected from the group consisting of styrene, vinyl chloride, vinyl 2-ethylhexanoate, vinyl laurate, vinyl stearate, vinyl neo-pentanoate, vinyl 2-ethylhexanoate, vinyl neo-nonanoate, vinyl neo-decanoate, vinyl neo-undecanoate, vinyl neo-dodecanoate, isobutyl vinyl ether, 2-chloroethyl vinyl ether, stearyl vinyl ether, n-butyl acrylate, isobutyl acrylate, sec-butyl acrylate, tert-butyl acrylate, n-pentyl acrylate, neopentyl acrylate, n-hexyl acrylate, n-heptyl acrylate, n-octyl acrylate, isooctyl acrylate, isononyl acrylate, n-decyl acrylate, isodecyl acrylate, 2-ethylhexyl acrylate, benzyl acrylate, oleyl acrylate, palmityl acrylate, stearyl acrylate, n-butyl methacrylate, isobutyl methacrylate, sec-butyl methacrylate, tert-butyl methacrylate, n-pentyl methacrylate, neopentyl methacrylate, n-hexyl methacrylate, n-heptyl methacrylate, n-octyl methacrylate, isooctyl methacrylate, isononyl methacrylate, n-decyl methacrylate, isodecyl methacrylate, 2-ethylhexyl methacrylate, benzyl methacrylate, oleyl methacrylate, palmityl methacrylate, stearyl methacrylate, unsaturated vinyl esters of (meth)acrylic acid such as those derived from fatty acids and fatty alcohols, monomers derived from cholesterol, vinyl chloride, 1-butene, 2-butene, 1-pentene, 1-hexene, 1-octene, isobutylene, isoprene, and combinations thereof.

Non-limiting examples of phosphorus-containing (meth) acrylate monomers may be found in the book "Phosphorus-Based Polymers: From Synthesis to Applications", Edited by Sophie Monge and Ghislain David (Royal Society of Chemistry, 2014), the relevant contents of which is herein incorporated by reference.

Non-limiting examples of (meth)acrylated fatty acid monomers derived from plant oils (e.g., soybean) may be found in *Polymer*, 2004, volume 45, 7729-7737, the relevant contents of which is herein incorporated by reference. Non-limiting examples of sugar acrylic monomers may be found in U.S. Pat. Nos. 8,871,512 and 3,356,652, the relevant contents of which are herein incorporated by reference.

In one non-limiting embodiment, the block copolymer according to the disclosed and/or claimed inventive concept(s) comprises at least one block A consisting of repeating units derived from at least one monomer $a_1$ comprising at least one functionalized or unfunctionalized acryloyl moiety and at least one lactam moiety; and at least one block B comprising repeating units derived from: at least one monomer selected from the group consisting of functionalized and unfunctionalized $C_{13}$-$C_{40}$ alkyl (meth)acrylic acids and salts thereof, $C_{13}$-$C_{40}$ alkyl (meth)acrylates, $C_{13}$-$C_{40}$ alkyl (meth)acrylamides, aralkyl (meth)acrylic acids and salts thereof, aralkyl (meth)acrylates, aralkyl (meth)acrylamides, and combinations thereof; and optionally, at least one monomer $a_2$ comprising at least one functionalized or unfunctionalized acryloyl moiety and at least one lactam moiety.

In another non-limiting embodiment, the block copolymer according to the disclosed and/or claimed inventive concept(s) comprises at least one block A consisting of repeating units derived from at least one monomer $a_1$ comprising at least one functionalized or unfunctionalized acryloyl moiety and at least one lactam moiety; and at least one block B comprising repeating units derived from: at least one monomer selected from the group consisting of functionalized and unfunctionalized $C_{13}$-$C_{40}$ alkyl (meth)acrylic acids and salts thereof, $C_{13}$-$C_{40}$ alkyl (meth)acrylates, $C_{13}$-$C_{40}$ alkyl (meth)acrylamides, aralkyl (meth)acrylic acids and salts thereof, aralkyl (meth)acrylates, aralkyl (meth)acrylamides, and combinations thereof; and at least one monomer $a_2$ comprising at least one functionalized or unfunctionalized acryloyl moiety and at least one lactam moiety.

In yet another non-limiting embodiment, the block copolymer according to the disclosed and/or claimed inventive concept(s) comprises:

(a) at least one block A consisting of repeating units derived from at least one monomer $a_1$ having a structure selected from the group consisting of:

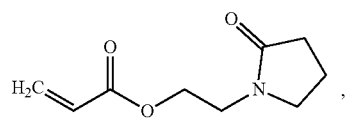

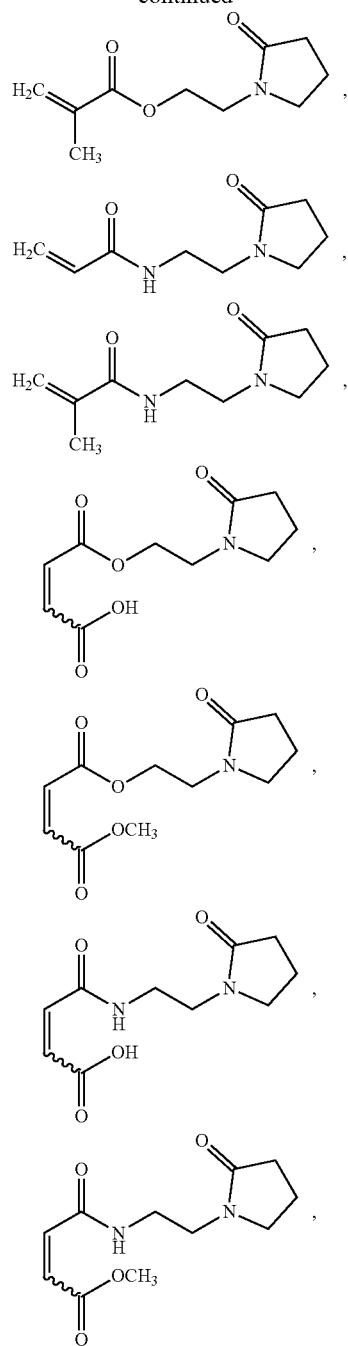

and combinations thereof; and, (b) at least one block B comprising repeating units derived from: at least one monomer selected from the group consisting of functionalized and unfunctionalized $C_{13}$-$C_{40}$ alkyl (meth)acrylic acids and salts thereof, $C_{13}$-$C_{40}$ alkyl (meth)acrylates, $C_{13}$-$C_{40}$ alkyl (meth)acrylamides, aralkyl (meth)acrylic acids and salts thereof, aralkyl (meth)acrylates, aralkyl (meth)acrylamides, and combinations thereof; and optionally, at least one monomer $a_2$ having a structure selected from the group consisting of:

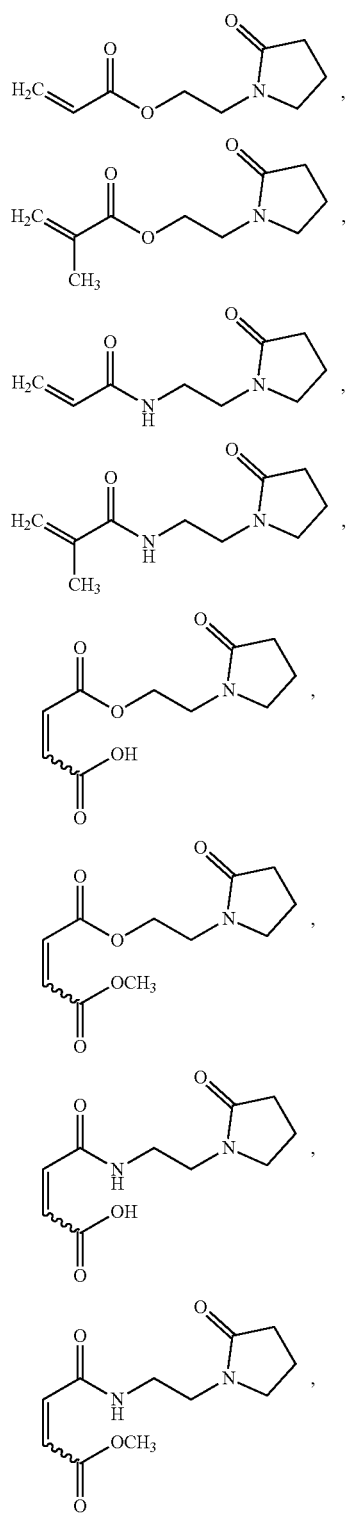
and combinations thereof.
In one non-limiting embodiment, the block copolymer according to the disclosed and/or claimed inventive concept(s) has a structure selected from the group consisting of:
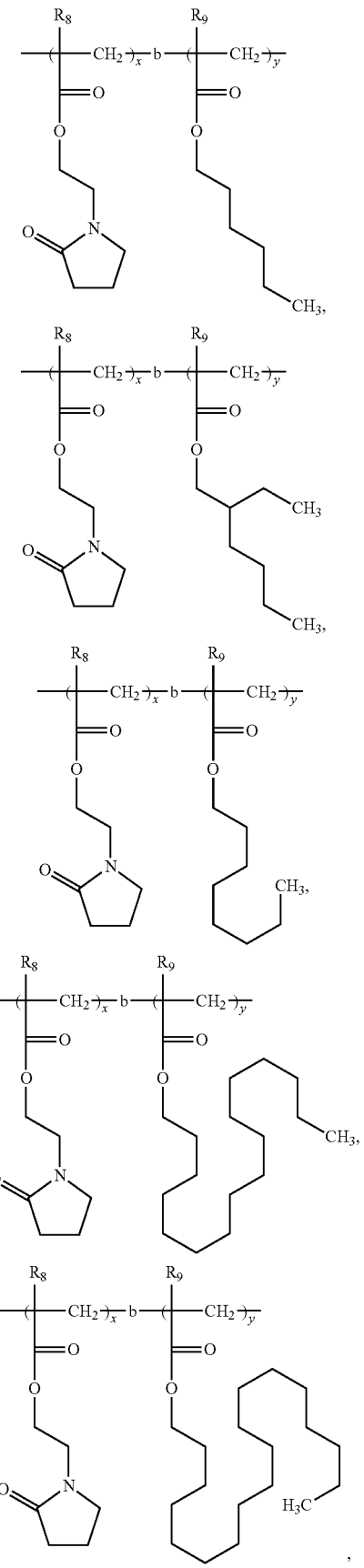

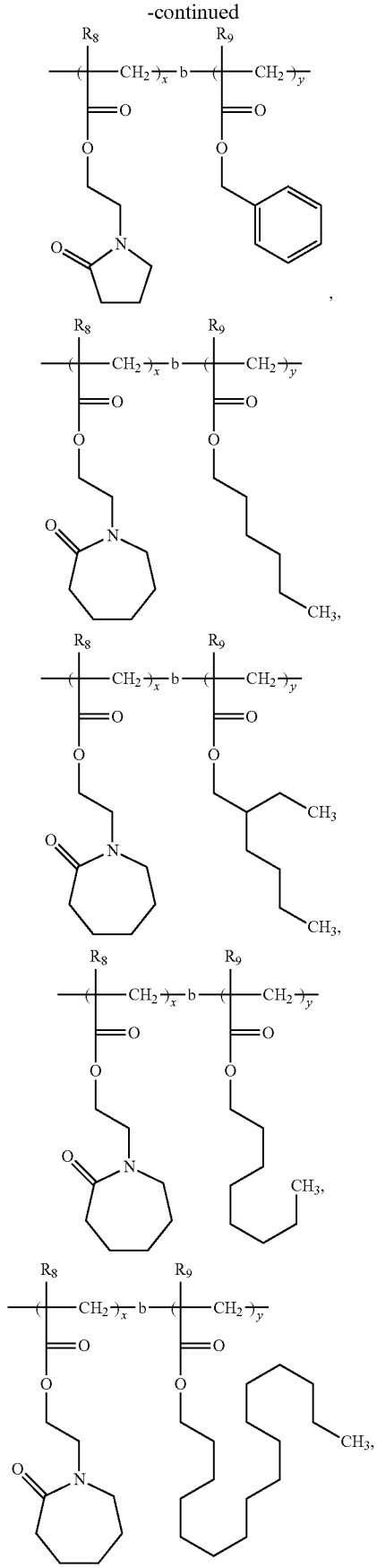

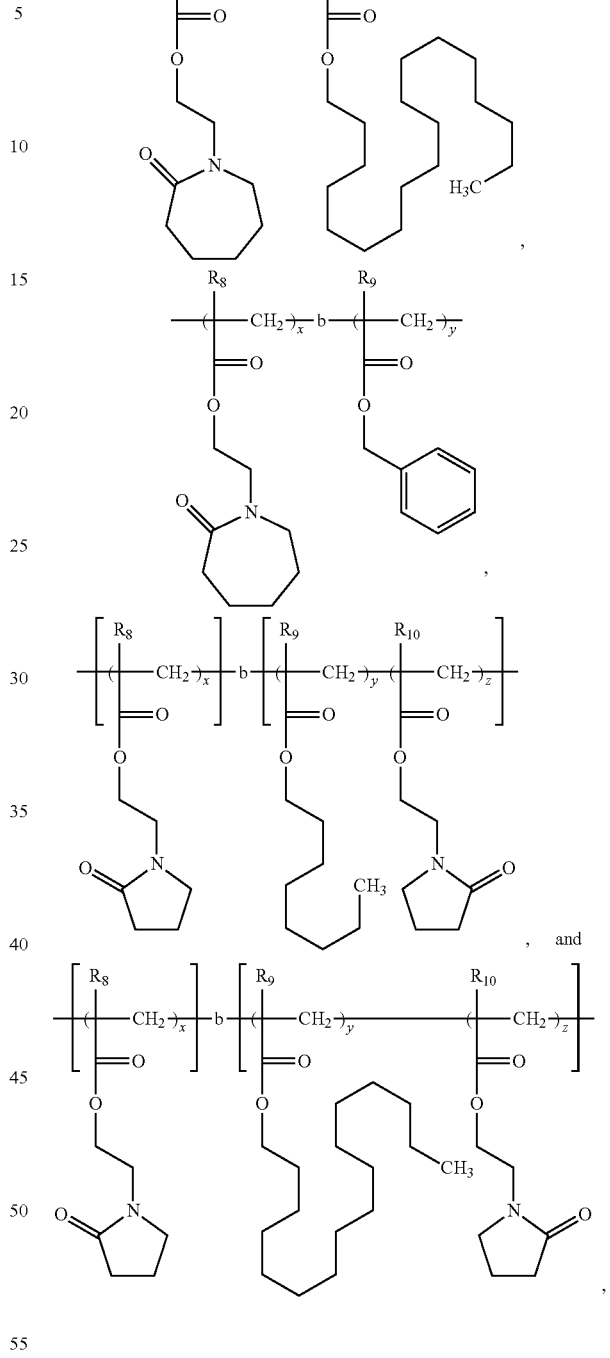

wherein each x and y is independently an integer having a value from about 10 to about 10000, z is an integer having a value from 0 to about 10000, and each $R_8$, $R_9$ and $R_{10}$ is independently selected from the group consisting of hydrogen, methyl, and combinations thereof.

In another non-limiting embodiment, the block copolymer according to the disclosed and/or claimed inventive concept(s) has a structure selected from the group consisting of:

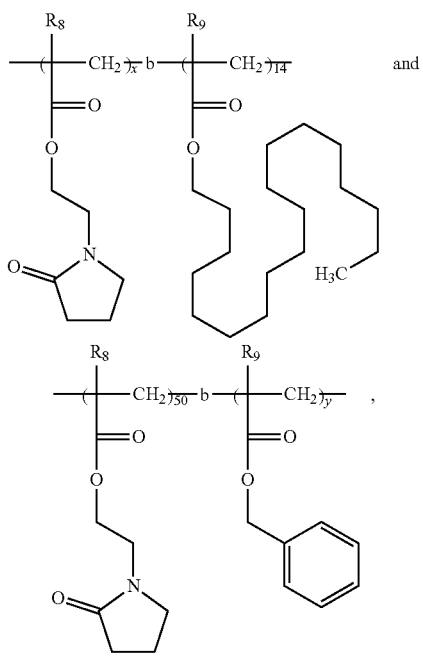

wherein x is an integer having a value from about 40 to about 1000, y is an integer having a value from about 50 to about 250, and each $R_8$ and $R_9$ is independently selected from the group consisting of hydrogen, methyl, and combinations thereof.

In one non-limiting embodiment, the repeating units derived from monomer $a_2$ may be present in an amount from about 1 to about 99 percent by weight of block B of the block copolymer. In another non-limiting embodiment, the repeating units derived from monomer $a_2$ may be present in an amount from about 1 to about 50 percent by weight of block B of the block copolymer. In yet another non-limiting embodiment, the repeating units derived from monomer $a_2$ may be present in an amount from about 1 to about 25 percent by weight of block B of the block copolymer.

In a second aspect, the disclosed and/or claimed inventive concept(s) provides a composition comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

In one non-limiting embodiment, the composition is a personal care composition, pharmaceutical composition, coating composition, construction composition, nutritional composition, agricultural composition, adhesive composition, oilfield composition, household, industrial and institutional composition, cementing fluid, servicing fluid, gravel packing mud, fracturing fluid, completion fluid, work-over fluid, spacer fluid, drilling mud, biocide, ink, paper, polish, membrane, metal working fluid, plastic, textile, printing composition, lubricant, detergent, battery composition, glass coating composition, or preservative composition. In another non-limiting embodiment, the composition is a personal care composition, pharmaceutical composition, coating composition, construction composition, nutritional composition, or an agricultural composition. In yet another non-limiting embodiment, the composition is a personal care composition.

In a third aspect, the disclosed and/or claimed inventive concept(s) provides a personal care composition comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

Non-limiting examples of personal care compositions include sun care compositions, face care compositions, lip care compositions, eye care compositions, skin care compositions, after-sun compositions, body care compositions, nail care compositions, anti-aging compositions, insect repellants, oral care compositions, deodorant compostions, hair care compositions, conditioning compositions, color cosmetic compositions, color-protection compositions, self-tanning compositions, and foot care compositions.

In one non-limiting embodiment, the personal care compositions may further comprise at least one additive selected from the group consisting of UV actives, UV active solubilizers, oils, waxes, solvents, emulsifiers, preservatives, antioxidants, antiradical protecting agents, vitamins, perfumes, insect repellants, dyes, pigments, humectants, fillers, thickeners, film formers, stabilizers, buffers, spreading agents, pearlizing agents, electrolytes, acids, bases, crystalline structuring agents, abrasives, pharmaceutically or cosmetically acceptable excipients, and combinations thereof.

In one non-limiting embodiment, the block copolymer that is a component of personal care compositions according to the disclosed and/or claimed inventive concept(s) is present in an amount from about 0.01% by weight to about 20% by weight of the composition. In another non-limiting embodiment, the block copolymer is present in an amount from about 0.1% by weight to about 10% by weight of the composition. In yet another non-limiting embodiment, the polymer is present in an amount from about 0.25% by weight to about 5.0% by weight of the composition.

Non-limiting applications of hair care compositions include hairstyle retention at high relative humidity, hair styling, hair setting, hair sculpting, hair curling, hair holding, hair waving, hair fixing, hair maintaining, hair shaping, hair straightening, hair volumizing, hair relaxing, shampooing, hair conditioning, hair cleansing, promoting hair style durability, imparting humidity resistance to hair and hair styles, enhancing hair shine, repairing split ends of hair, enhancing hair manageability such as lightness, smoothness, softness, disentangling and/or suppleness of hair, modulating hair stylability, protecting hair from thermal damage, hair dyeing, hair coloring, hair bleaching, oxidation dyeing of hair, limiting hair color bleeding, protecting hair color, hair treating (e.g., anti-dandruff), anti-hair fall, and/or protecting hair from UV radiation.

Non-limiting examples of hair care compositions include shampoos, conditioners, aerosols, mousses, sprays, mists, gels, waxes, creams, lotions, glues, pomades, spritzes, solutions, oils, liquids, solids, W/O emulsions, O/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

Non-limiting examples of suitable UV actives include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomenthyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; n-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor, glyceryl ethylhexanoate dimethoxycinnamate; 1,3-bis-[(2'-cyano-3',3'-diphenylacryloyl)oxy]-2,2-bis-{[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl) aminobenzoate; 6-tert-butyl-2-(5-chloro-2H-benzotriazole-2-yl)-4-methylphenol; p-aminobenzoic acid; 3,3',3",5,5',5"-hexa-tert-butyl-α-α'-α"-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor, terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Any range of composition pH may be used. In aspects wherein the composition may be applied to keratinous material, the pH may range from about 2 to 12. The pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, α-hydroxyacids, β-hydroxyacids, α,β-hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

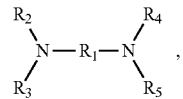

wherein $R_1$ may be a propylene residue that may be optionally substituted with an hydroxyl group or a $C_1$-$C_4$ alkyl radical; $R_2$, $R_3$, $R_4$ and $R_5$ are identical or different and represent a hydrogen atom, a $C_1$-$C_4$ alkyl radical or $C_1$-$C_4$ hydroxyalkyl radical.

The personal care compositions may additionally comprise one or more buffers. Suitable buffering agents include, but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate.

The personal care compositions may be formulated in any of the product forms known to a person of ordinary skill in the art. Non-limiting product forms are described below.

Product Forms

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, O/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The compositions may also take the form of skin-washing compositions, and in the form of solutions or gels for the bath or shower, or of make-up removal products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, home-manicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP556660; EP661037; EP661038; EP662315; EP676194; EP796077; EP970682; EP976383; EP1415654; and EP2067467; and WO2005/032506; each of which is herein incorporated in its entirety by reference.

It is also contemplated that the personal care compositions may be used in products for male and/or female personal grooming and/or toiletry such as: sanitary napkins, baby diapers, adult diapers, feminine products, products for incontinence, and other related products.

An array of additional personal care compositions, methods, and uses are contemplated. Disclosure of these compositions may be found in the following brochures by Ashland Specialty Ingredients, each of which is herein incorporated in its entirety by reference: *Plasdone™ K-29/ 32, Advanced non-oxidative, non-abrasive teeth whitening in toothpastes, mouthwashes, and oral rinses* (2010), *Polymers for oral care, product and applications guide* (2002), *A composition guide for excellent hair styling gels and lotions* (April 2003), *PVP (polyvinylpyrrolidone)* (no date provided), and *Textile chemicals, solutions for the most challenging product environment* (no date provided).

Also contemplated are personal care compositions described in the publications listed below, each of which is herein incorporated in its entirety by reference: (1) Prototype Compositions—Personal Care Products (2009) from Xiameter, Dow Corning. (2) Sun care compositions under the category "Refreshing Sun", "Younger Sun", "Sun for Men", and "Sunny Glow" from Dow Corning. (3) Cosmetic Nano-technology, Polymers and Colloids in Cosmetics, 2007, ACS Symposium Series. (4) Review Paper. Lipid nanoparticles (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polyglycerol esters), antiperspirants (including, but not limited to aluminium chlorohydrates, aluminium zirconium chlorhydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin lighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip- .com, the contents of each of these disclosures are herein incorporated in their entirety by reference.

Further reference to formulary co-ingredients and product forms include the disclosures in US 2010/0183532, paragraphs [0096]-[0162], and WO 2010/105050, paragraphs [0053]-[0069], the contents of which are herein incorporated in their entirety by reference.

Any known conditioning agent may be used in the personal care compositions. An extensive discussion on conditioning agents may be found in the book *Conditioning Agents for Skin and Hair, Cosmetic Science and Technology Series*, Volume 21, 1999, Marcel Dekker Publishers. The contents of the book are herein incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, ceramide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of eucalyptus, lavender, vetiver, litsea cubeba, lemon, sandalwood, rosemary, chamomile, savory, nutmeg, cinnamon, hyssop, caraway, orange, geranium, cade, bergamot, and blends thereof.

The conditioning agent may be a fluorinated or a perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl (C1-C20) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or microemulsions.

The cationic polymers that may be used as conditioning agents generally have a molecular weight (average number) from about 500 Da to about 5,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat™ by Ashland Specialty Ingredients; terpolymers of dimethyl amino ethyl methacrylate, vinyl caprolactam, and vinyl pyrrolidone such as the product sold under the name Gaffix™ VC 713 by Ashland Specialty Ingredients; the vinyl pyrrolidone/methacrylamidopropyl dimethylamine copolymer, marketed under the name Styleze™ CC 10 by Ashland Specialty Ingredients; and the vinyl pyrrolidone/quaternized dimethyl amino propyl methacrylamide copolymers such as the product sold under the name Gafquat™ HS 100 by Ashland Specialty Ingredients (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl, and blends thereof.

Non-limiting examples of suitable hydrolyzed cationic proteins include: Croquat® L, in which the quaternary ammonium groups include a $C_{12}$ alkyl group, Croquat® M, in which the quaternary ammonium groups include $C_{10}$-$C_{18}$ alkyl groups, Croquat® S in which the quaternary ammonium groups include a $C_{18}$ alkyl group, Crotein® Q in which the quaternary ammonium groups include at least one $C_1$-$C_{18}$ alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, n-stearoyl phytosphingosine, 2-N-palmitoyl amino-hexadecane-1,3-diol, bis-(N-hydroxy ethyl n-cetyl) malonamide, n-(2-hydroxy ethyl)-N-(3-cetoxyl-2-hydroxy propyl) amide of cetylic acid, n-docosanoyl n-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imadazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetra-carboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), n-Hance™ SP-100 (INCI Name: acrylamidopropyl trimonium chloride/acrylamide copolymer), and n-Hance™ cationic guar (INCI Name: guar hydroxypropyltrimonium chloride) from Ashland Specialty Ingredients (2) Salcare® from BASF Corp.

(3) Softcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

(6) Conditioneze™ 7 and Conditioneze™ NT-20 from Ashland Specialty Ingredients (Wayne, N.J.).

Of course, mixtures of two or more conditioning agents may be used.

In one non-limiting embodiment, the conditioning agent(s) may be present in an amount from about 0.001% to about 20%. In another non-limiting embodiment, the conditioning agent(s) may be present in an amount from about 0.01% to about 10%. In yet another non-limiting embodiment, the conditioning agent(s) may be present in an amount from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bis-biquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, n-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In non-limiting aspects, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In non-limiting aspects, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled Minerals for personal care from Imerys Performance Minerals, the disclosure of which is herein incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl®; performance concentrates, under the trade names Sulfochem™ and Chemoryl; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is herein incorporated in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. In one non-limiting embodiment, the washing base may be present in an amount from about 4% to about 50% by weight.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer, acrylamides copolymer, acrylamide/sodium acrylate copolymer, acrylamide/sodium acryloyldimethyltaurate copolymer, acrylates/acetoacetoxyethyl methacrylate copolymer; acrylates/beheneth-25 methacrylate copolymer, acrylates/C10-C30 alkyl acrylate crosspolymer, acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer, acrylates/steareth-20 methacrylate copolymer; acrylates/stearyl methacrylate copolymer; acrylates/vinyl isodecanoate crosspolymer, acrylic acid/acrylonitrogens copolymer, adipic acid/methyl DEA crosspolymer, agar, agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer, ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *Arachis hypogaea* (peanut) flour, ascorbyl methylsilanol pectinate; astragalus gummifer gum; attapulgite; *Avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer, calcium starch octenylsuccinate; C20-40 alkyl stearate; canolamidopropyl betaine; capramide DEA; capryl/capramidopropyl betaine; carbomer, carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar, carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked bacillus/glucose/sodium glutamate ferment; cyamopsis tetragonoloba (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer, dimethicone/PEG-15 crosspolymer, dimethicone propyl PG-betaine; dimethylacrylamide/acrylic acid/polystyrene ethyl methacrylate copolymer; dimethylacrylamide/sodium acryloyldimethyltaurate crosspolymer, disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour, guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer, hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer, hydroxypropyl guar, hydroxypropyl methylcellulose; hydroxypropyl methylcellulose stearoxy ether, hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether, lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™ MG copolymer; PEG-10/lauryl dimethicone crosspolymer, PEG-15/lauryl dimethicone crosspolymer, PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™ MG copolymer, PEG-150 pentaerythrityl tetrastearate; PEG-4 rapeseedamide; PEG-150/stearyl alcohol/SMDI copolymer, phaseolus angularis seed powder, polianthes tuberosa extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer, potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; pyrus cydonia seed; pyrus malus (apple) fiber, rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; rosa multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer, sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer, sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *Solanum tuberosum* (potato) starch; soyamide DEA; soyamidopropyl betaine; starch/acrylates/acrylamide copolymer, starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether, steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer, TEA-hydrochloride; trideceth-2 carboxamide MEA; tridecyl alcohol; triethylene glycol dibenzoate; trimethyl pentanol hydroxyethyl ether, *Triticum vulgare* (wheat) germ powder; *Triticum vulgare* (wheat) kernel flour, *Triticum vulgare* (wheat) starch; tromethamine acrylates/acrylonitrogens copolymer, tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *Zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurfr™ cetyl modified hydroxyethylcellulose, n-Hance™ cationic guar, n-Hance™ HP Series hydroxypropyl guar, n-Hance™ SP-100 conditioning polymer, and Supercol™ guar gum from Ashland Specialty Ingredients (2) Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze™, Rapithix™ A-60, Rapithix™ A-100, Ultrathix™ P-100, Lubrajel™ and FlexiThix™ from Ashland Specialty Ingredients (Wayne, N.J.).

Also suitable as a thickener/rheology modifier are lightly- to moderately-crosslinked polyvinylpyrrolidones. Disclosures of these polymers are provided in the following publications, each of which is herein incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in *Chemistry and Biology*; volume 3, 2010.

Also contemplated are additional personal care compositions that may comprise the polymers described herein. Disclosures on such compositions may be found in the publications listed below, each of which is herein incorporated in its entirety by reference: (1) Prototype Compositions—Personal Care Products (2009) from Xiameter, Dow Corning. (2) Sun care compositions under the category "Refreshing Sun", "Younger Sun", "Sun for Men", and "Sunny Glow" from Dow Corning. (3) Cosmetic Nanotechnology, Polymers and Colloids in Cosmetics, 2007, ACS Symposium Series. (4) Review Paper: Lipid nanoparticles (SLN, NLC) in cosmetic and pharmaceutical dermal products, International Journal of Pharmaceutics, Volume 366, 2009.

Non-limiting examples of properties that may be beneficially modified by the block copolymers and compositions disclosed herein are solution viscosity, rheology, thickening, film formation, lubricity, gloss, adhesion, impact resistance, fluid snap, film brittleness, film toughness, coating hardness, water resistance, tack, surface gloss and shine, surface tension, wetting, foaming and foam stabilization, tensile strength, solvency, solubilization speed, compatibility, bioadhesion, particulate suspension, particulate dispersive properties, dispersive properties, delivery of hydrophobic compositions, formulation stabilization, flexibility, chemical resistance, abrasion resistance, penetration, and combinations thereof.

In a fourth aspect, the disclosed and/or claimed inventive concept(s) provides a composition in the form of colloidal particles comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

In one non-limiting embodiment, the colloidal particles have spherical morphologies. In another non-limiting embodiment, the colloidal particles have non-spherical morphologies. Non-limiting examples of colloidal particles having non-spherical morphologies include worms and vesicles. Further insight into the structure and properties of colloidal particles having non-spherical morphologies may be found in the publication *J. Am. Chem. Soc.*, 2014, volume 136, 10174-10185, the contents of which are herein incorporated in its entirety be reference.

In one non-limiting embodiment, the colloidal particles have a mean diameter ranging from about 10 nanometers to about 1000 nanometers, as measured by a suitable technique such as, for example, Dynamic Light Scattering. In another non-limiting embodiment, the colloidal particles have a mean diameter ranging from about 25 nanometers to about 750 nanometers. In yet another non-limiting embodiment, the colloidal particles have a mean diameter ranging from about 50 nanometers to about 500 nanometers.

In a fifth aspect, the disclosed and/or claimed inventive concept(s) provides a Pickering emulsion composition comprising a block copolymer comprising at least one block A consisting of repeating units derived from at least one monomer $a_1$ comprising at least one functionalized or unfunctionalized acryloyl moiety and at least one lactam moiety, and at least one block B comprising repeating units derived from at least one hydrophobic monomer $b_1$ and optionally, at least one monomer $a_2$ comprising at least one functionalized or unfunctionalized acryloyl moiety and at least one lactam moiety, with the proviso that the monomer $b_1$ is not lauryl (meth)acrylate.

Pickering emulsions are emulsions of any type, either oil-in-water (o/w), water-in-oil (w/o), or even multiple, stabilized by solid particles in place of surfactants. Pickering emulsions retain the basic properties of classical emulsions stabilized by surfactants (emulsifiers), so that a Pickering emulsion can be substituted for a classical emulsion in most applications of emulsions. The stabilization by solid particles brings about specific properties to such emulsions. The high resistance to coalescence is a major benefit of the stabilization by solid particles. The 'surfactant-free' character makes them attractive to several applications fields, non-limiting examples of which include cosmetic and pharmaceutical applications where surfactants often show adverse effects. Solid stabilizing particles are necessarily smaller than emulsion droplets. Solid particles of nanometric size (or sub-micron, ~100 nanometers) allow the stabilization of droplets as small as few micrometers diameter; stabilization of larger droplets is possible as well. Micron-sized solid particles can stabilize larger droplets, the diameter of which possibly reaching few millimeters. The availability of stable millimeter-sized emulsions is a supplementary benefit of Pickering emulsions with respect to classical emulsions; this possibility comes from their high stability against coalescence.

Properties and applications of Pickering emulsions in general are described by Chevalier and Bolzinger in *Colloids and Surfaces A: Physicochemical and Engineering Aspects,* 2013, volume 439, 23-34, the contents of which are herein incorporated in its entirety by reference.

In one non-limiting embodiment, the block copolymer that is a component of Pickering emulsion compositions according to the disclosed and/or claimed inventive concept (s), is present in an amount from about 0.01% by weight to about 20% by weight of the composition. In another non-limiting embodiment, the block copolymer is present in an amount from about 0.1% by weight to about 10% by weight of the composition. In yet another non-limiting embodiment, the block copolymer is present in an amount from about 0.25% by weight to about 5.0% by weight of the composition.

In one non-limiting embodiment, the block copolymer is present in the form of colloidal particles in the Pickering emulsion composition. In another non-limiting embodiment, the block copolymer is present in the form of spherical colloidal particles in the Pickering emulsion composition.

In one non-limiting embodiment, the composition comprising the block copolymers according to disclosed and/or claimed inventive concepts is a hydrogel. Further insights into the properties and applications of hydrogels may be found in the review article by Ullah and coworkers in *Materials Science and Engineering C,* 2015, volume 57, 414-433 the contents of which are herein incorporated in its entirety by reference.

Methods of Synthesis

Reversible addition-fragmentation chain transfer (RAFT) polymerization is one of the most robust and versatile methods for providing living characteristics to radical polymerization. With appropriate selection of the RAFT agent for the monomers and reaction conditions, it is applicable to the majority of monomers subject to radical polymerization. The process can be used in the synthesis of well-defined homo-, gradient, diblock, triblock, and star polymers and more complex architectures, which include microgels and polymer brushes.

When preparing, for example, a block copolymer in the presence of the control agent, the end of the growing block is provided with a specific functionality that controls the growth of the block by means of reversible free radical deactivation. The functionality at the end of the block is of such a nature that it can reactivate the growth of the block in a second and/or third stage of the polymerization process with other ethylenically unsaturated monomers providing a covalent bond between, for example, a first and second block [A] and [B] and with any further optional blocks.

Further details on the chemistry of synthesis of block copolymers by RAFT processes may be found in the following publications, each of which is herein incorporated in its entirety by reference: *Polymer,* 2008, volume 49, 1079-1131; *Chemical Society Reviews,* 2014, volume 43, 496-505; *Macromolecules,* 1998, volume 31, 5559-5562; and *Polymer,* 2013, volume 54, 2011-2019.

In one non-limiting embodiment, the block copolymer according to the disclosed and/or claimed inventive concepts is obtained by RAFT-mediated controlled radical polymerization. In one non-limiting embodiment, the reversible transfer agents may be one or more compounds selected from the group consisting of dithioesters, thioethers-thiones, trithiocarbonates, dithiocarbamates, xanthates and mixtures thereof.

In one non-limiting embodiment, the average degree of polymerization (DP) for block A of the block copolymer is a value ranging from about 5 to about 500,000. In another non-limiting embodiment, the average DP for the block A is a value ranging from about 5 to about 50,000. In yet another non-limiting embodiment, the average DP for the block A is a value ranging from about 10 to about 10,000.

In one non-limiting embodiment, the average DP for block B is a value ranging from about 10 to about 100,000. In another non-limiting embodiment, the average DP for the block B is a value ranging from about 10 to about 10,000. In yet another non-limiting embodiment, the average DP for the block B is a value ranging from about 10 to about 1000.

The block copolymers according to the disclosed and/or claimed inventive concept(s) may be prepared according to the examples set out below. These examples are presented herein for purposes of illustration of the disclosed and/or claimed inventive concept(s) and are not intended to be limiting, for example, the preparations of the polymers. In the examples, the following abbreviations are used:

NMEP: N-2-(methacryloyloxy)ethyl pyrrolidone
SMA: Stearyl (meth)acrylate
BzMA: Benzyl (meth)acrylate
CDB: Cumyl dithiobenzoate
CPDB: 2-Cyano-2-propyl dithiobenzoate
AVCA: 4,4'-azobis(4-cyanopentanoic acid)
TBPE: tert-butyl peroxy-2-ethylhexanoate
AIBN: Azoisobutyronitrile
CTA: Chain transfer agent
DLS: Dynamic light scattering
GPC: Gel permeation chromatography
TEM: Transmission electron microscopy
SEM: Scanning electron microscopy
PISA: Polymerization Induced Self Assembly
DP: Degree of polymerization
PMMA: Poly(methyl)methacrylate
$M_n$: Number-average molecular weight
$M_w$: Weight-average molecular weight

EXAMPLES

Example 1: Synthesis of Poly(SMA)$_{14}$-Poly(NMEP)$_{98}$ Diblock Copolymer

Part A: Preparation of Poly(SMA)$_{14}$ Macro-CTA

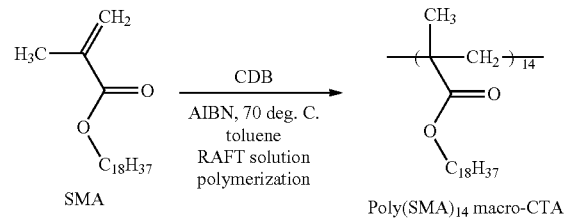

SMA (33.4765 g, 0.099 mol), CDB RAFT agent (5.1690 g, 19 mmol; target degree of polymerisation, DP=5) and AIBN (0.6233 g, 3.8 mmol; CTA/initiator molar ratio=5.0) were weighed into a 250 ml round-bottomed flask. Toluene (58 ml) was deoxygenated separately with nitrogen for 30 min prior to addition to the other reagents. The reaction solution was stirred and degassed in an ice bath for a further 30 min, before placing in an oil bath at 70° C. The polymerization was allowed to proceed for 10 h, resulting in a final monomer conversion of 80% as judged by $^1$H NMR. The crude homopolymer was purified by precipitating into a ten-fold excess of ethanol. This purification step was repeated twice to afford a pure Poly(SMA) macro-CTA (21.6 g, <1% residual monomer). The mean degree of polymerization was calculated to be 14, as judged by $^1$H NMR spectroscopy. GPC analysis using a 3:1 v/v chloroform/methanol mixed eluent indicated an $M_n$ of 7500 g mol$^{-1}$ and an $M_w/M_n$ of 1.12 (vs. a series of near-mono-disperse PMMA calibration standards).

Part B: Synthesis of Poly(SMA)$_{14}$-Poly(NMEP)$_{98}$ Diblock Copolymer

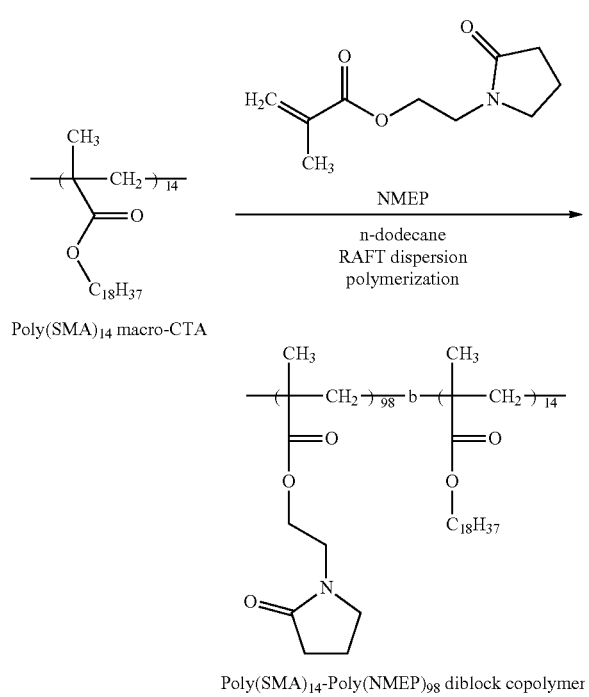

Poly(SMA)$_{14}$ macro-CTA

Poly(SMA)$_{14}$-Poly(NMEP)$_{98}$ diblock copolymer

A typical protocol for the synthesis of Poly(SMA)$_{14}$-Poly(NMEP)$_{98}$ diblock copolymer nanoparticles was as follows: Poly(SMA)$_{14}$ macro-CTA (0.0706 g), NMEP (0.2787 g, 1.413 mmol; target DP=100), TBPE (0.755 mg, 3.49 μmol; dissolved at 10% v/v in n-dodecane; CTA/TBPE molar ratio=4.0) were dissolved in n-dodecane (4.1 ml, 10% w/w) in a 25 ml round-bottomed flask. The reaction mixture was sealed and purged with nitro-gen for 30 minutes, prior to immersion in an oil bath set at 90° C. for 2 h. The resulting copolymer was analysed by GPC using a 3:1 chloroform/methanol mixed eluent ($M_n$=49 600 g mol$^{-1}$, $M_w/M_n$=1.19 vs. PMMA standards). $^1$H NMR spectroscopy analysis of the final reaction solution diluted approximately ten-fold in CDCl$_3$ indicated 98% NMEP conversion. DLS studies conducted on a 0.20% w/w copolymer dispersion indicated an intensity-average particle diameter of 36 nm (DLS polydispersity, PDI=0.01).

Example 2—Example 14: Synthesis of Poly(SMA)$_{14}$-Poly(NMEP)$_x$ Diblock Copolymers Utilising the kinetic data from Example 1, a series of Poly(SMA)$_{14}$-Poly(NMEP)$_x$ diblock copolymers were prepared (x being the DP of the NMEP block) at 10% w/w solids. The target DP for the PNMEP core-forming block (x) was systematically varied from 50 to 1000 and relatively high (>96%) NMEP conversions were achieved in all cases. The summary of results is shown in Table 1. Poly(SMA)$_{14}$-Poly(NMEP) diblock copolymers with a target Poly(NMEP) DP (x) of less than 250 were analyzed by GPC. All Poly(SMA)$_{14}$-Poly(NMEP)$_x$ diblock copolymers exhibited high blocking efficiencies relative to the Poly(SMA)$_{14}$ macro-CTA and the copolymer $M_n$ increased as higher Poly(NMEP) DPs were targeted, as expected.

TABLE 1

Conversions, molecular weights ($M_n$), polydispersities ($M_w/M_n$) and mean DLS diameters obtained for Poly(SMA)$_{14}$-poly(NMEP)$_x$ (deonted by S$_{14}$-N$_x$ for brevity) diblock copolymer nanoparticles prepared at 10% w/w solids content.

| Example | Diblock Composition | Conversion[a] (%) | GPC[b] Mn (kg mol$^{-1}$) | $M_w/M_n$ | DLS particle diameter[c] (nm) |
|---|---|---|---|---|---|
| 2 | S$_{14}$-N$_{49}$ | 98 | 30.1 | 1.15 | 23 (0.205) |
| 3 | S$_{14}$-N$_{74}$ | 99 | 40.5 | 1.14 | 30 (0.028) |
| 4 | S$_{14}$-N$_{124}$ | 99 | 60.1 | 1.19 | 42 (0.034) |
| 5 | S$_{14}$-N$_{149}$ | 99 | 72.5 | 1.36 | 47 (0.054) |
| 6 | S$_{14}$-N$_{168}$ | 96 | 83.8 | 1.63 | 56 (0.008) |
| 7 | S$_{14}$-N$_{198}$ | 99 | 95.0 | 1.64 | 62 (0.015) |
| 8 | S$_{14}$-N$_{216}$ | 96 | 107.0 | 1.92 | 76 (0.025) |
| 9 | S$_{14}$-N$_{245}$ | 98 | 109.8 | 2.85 | 95 (0.005) |
| 10 | S$_{14}$-N$_{270}$ | 98 | Not determined | Not determined | 153 (0.006) |
| 11 | S$_{14}$-N$_{291}$ | 97 | Not determined | Not determined | 173 (0.006) |
| 12 | S$_{14}$-N$_{392}$ | 98 | Not determined | Not determined | 274 (0.028) |
| 13 | S$_{14}$-N$_{485}$ | 97 | Not determined | Not determined | 340 (0.035) |
| 14 | S$_{14}$-N$_{960}$ | 96 | Not determined | Not determined | 462 (0.010) |

[a] Monomer conversion determined by $^1$H NMR spectroscopy in CDCl$_3$
[b] Determined by 3:1 v/v chloroform/methanol GPC against PMMA calibration standards using a refractive index detector
[c] The number in brackets refers to the DLS polydispersity

Example 15: Synthesis of Poly(NMEP)$_{50}$-Poly(BzMA)$_{47}$ Diblock Copolymer Part A: Preparation of Poly(NMEP)$_{50}$ Macro-CTA

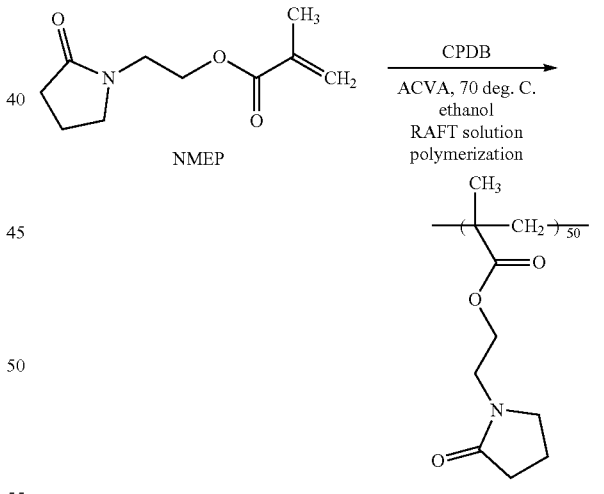

Poly(NMEP)$_{50}$ macro-CTA

NMEP (33.4012 g, 0.17 mol), CPDB RAFT agent (1.0006 g, 4.52 mmol; target DP=45), ACVA (337.8 mg, 1.21 mmol; CPDB/ACVA molar ratio=3.0) and ethanol (22.2815 g, 60% w/w solids) were weighed into a 250 ml round-bottom flask. The reaction solution was stirred and degassed in an ice bath for 45 min before being placed in an oil bath at 70° C. The polymerization was allowed to proceed for 5.75 h, resulting in a monomer conversion of 91% as judged by $^1$H NMR. The crude homopolymer was purified by precipitating into a ten-fold excess of diethyl ether. This purification protocol was repeated twice. The purified Poly(NMEP) macro-CTA was dissolved in the minimum volume of water and this concentrated aqueous solution was freeze-dried overnight to afford a pure Poly(NMEP) macro-CTA (<1% residual monomer). The mean degree of polymerization was calculated using $^1$H NMR to be 50. DMF GPC analysis indicated a $M_n$ of 8,000 g mol$^{-1}$ and a $M_w/M_n$ of 1.15 (compared to a series of near-monodisperse PMMA calibration standards).

Part B: Synthesis of Poly(NMEP)$_{50}$-Poly(BzMA)$_{47}$ Diblock Copolymer

Example 16: Synthesis of Poly(NMEP)$_{50}$-Poly(BzMA)$_{200}$ Diblock Copolymer Part A: Preparation of Poly(NMEP)$_{50}$ Macro-CTA

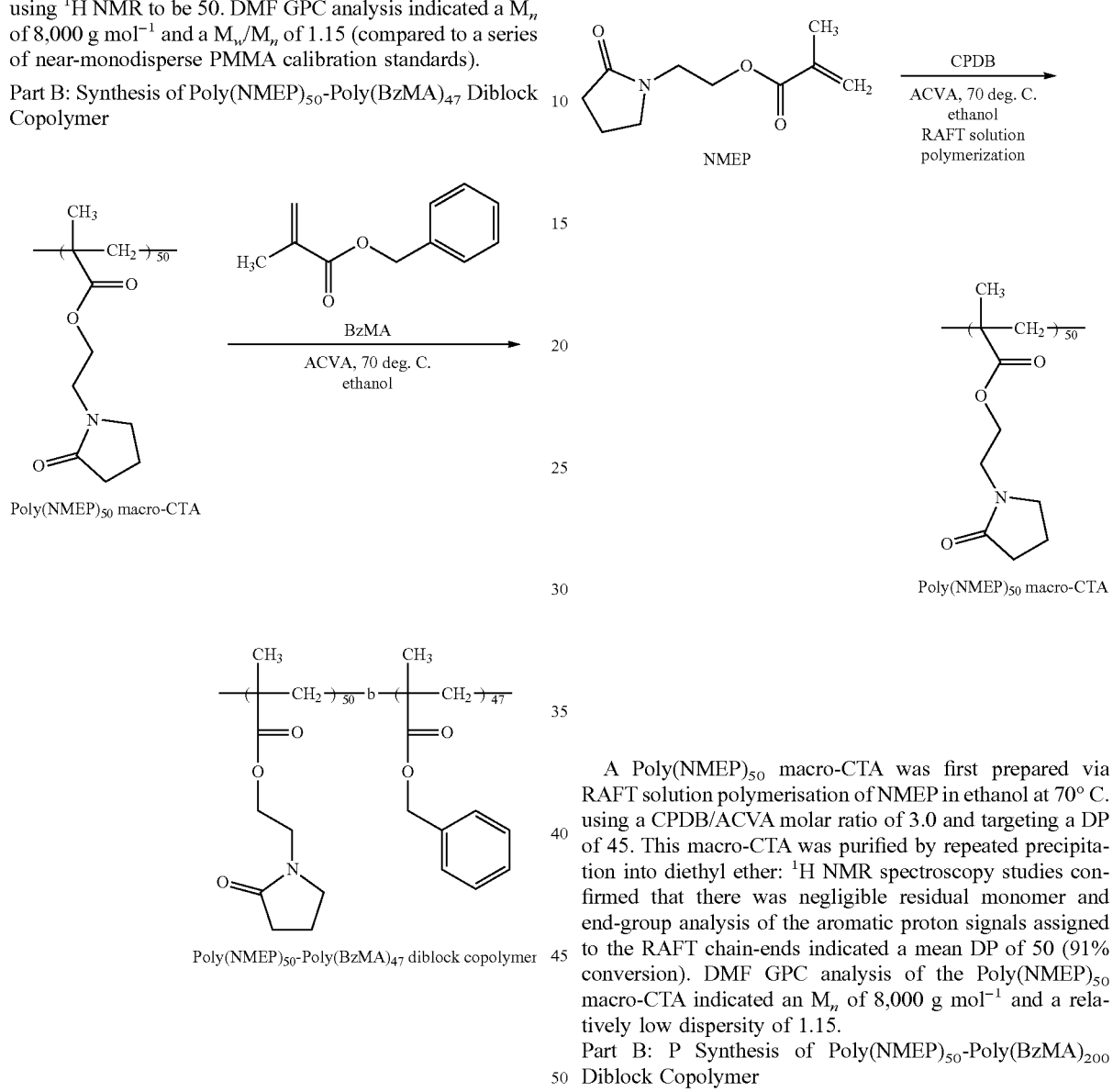

A Poly(NMEP)$_{50}$ macro-CTA was first prepared via RAFT solution polymerisation of NMEP in ethanol at 70° C. using a CPDB/ACVA molar ratio of 3.0 and targeting a DP of 45. This macro-CTA was purified by repeated precipitation into diethyl ether: $^1$H NMR spectroscopy studies confirmed that there was negligible residual monomer and end-group analysis of the aromatic proton signals assigned to the RAFT chain-ends indicated a mean DP of 50 (91% conversion). DMF GPC analysis of the Poly(NMEP)$_{50}$ macro-CTA indicated an $M_n$ of 8,000 g mol$^{-1}$ and a relatively low dispersity of 1.15.

Part B: P Synthesis of Poly(NMEP)$_{50}$-Poly(BzMA)$_{200}$ Diblock Copolymer

An amount of Poly(NMEP)$_{50}$ macro-CTA (0.3607 g) obtained according to Part A, BzMA (0.3124 g, 1.77 mmol; target DP=50) and ACVA (2.0 mg, 7.13 μmol; macro-CTA/ACVA molar ratio=5.0) were dissolved in ethanol (2.6948 g, 20% w/w) in a 14 ml vial. The reaction mixture was sealed and purged in an ice bath with nitrogen for 30 min, prior to immersion in an oil bath set at 70° C. for 24 h. The resulting crude copolymer was analysed by DMF GPC ($M_n$=12 000 g mol$^{-1}$, $M_w/M_n$=1.20). $^1$H NMR spectroscopy analysis of the final reaction solution (diluted in CDCl$_3$) indicated 94% BzMA conversion. Other diblock copolymer compositions were obtained by systematically adjusting the BzMA/Poly(NMEP)$_{50}$ macro-CTA molar ratio to give target Poly(BzMA) DPs ranging from 50 to 250.

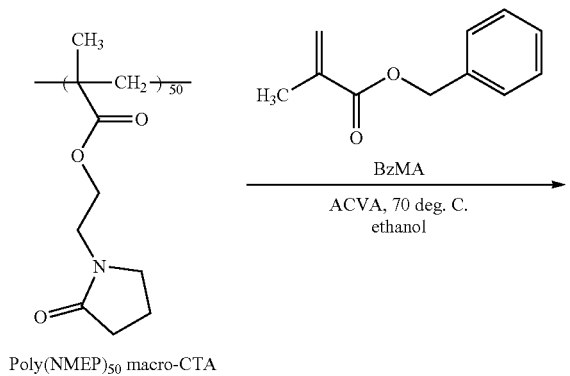

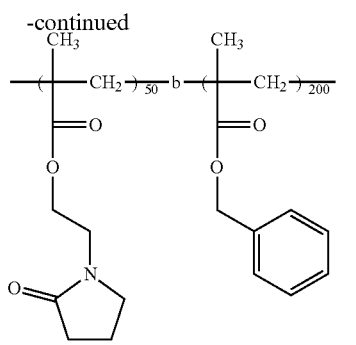

Poly(NMEP)₅₀-Poly(BzMA)₂₀₀ diblock copolymer

Poly(NMEP)₅₀ macro-CTA obtained according to Part A was subsequently utilized for the synthesis of Poly(NMEP)₅₀-poly(BzMA)₂₀₀ diblock copolymer nanoparticles via RAFT alcoholic dispersion polymerisation of BzMA. $^1$H NMR confirmed that 90% conversion was achieved within 12 h. Relatively low dispersities of less than 1.20 were obtained throughout the BzMA polymerisation, with a final $M_w/M_n$ of 1.17 being obtained after 24 h (94% conversion).

Example 17—Example 23: Synthesis of Poly(NMEP)₅₀-Poly(BzMA): Diblock Copolymers Utilising the kinetic data from Example 16, a series of Poly(NMEP)₅₀-poly(BzMA)$_x$ diblock copolymers were prepared (x being the DP of the BzMA block). The summary of results is shown in Table 2. All syntheses were conducted at 20% w/w solids and allowed to proceed for 24 h at 70° C. The target Poly(BzMA) DP was varied from 50 to 250 and at least 90% conversion was achieved in all cases as judged by $^1$H NMR spectroscopy. Each diblock copolymer was analysed by DMF GPC. High blocking efficiencies and low dispersities ($M_w/M_n$<1.23) were obtained, indicating the formation of well-defined block copolymers.

Example 24: Synthesis of Poly(NMEP)₄₇-Poly(BzMA)₂₄₃ Diblock Copolymer Nano-Objects Via a One-Pot PISA Protocol

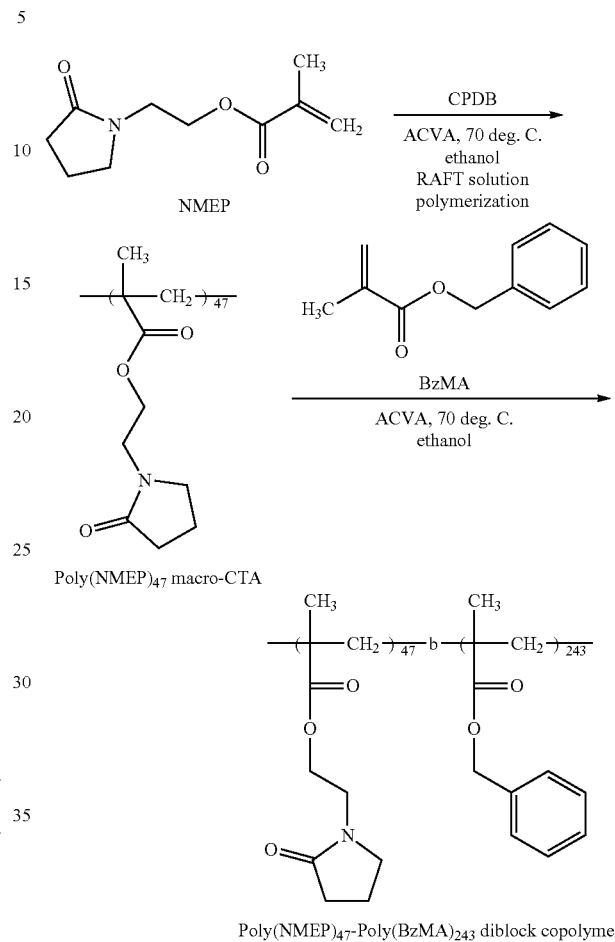

Poly(NMEP) macro-CTA was synthesised at 70° C. by targeting a DP of 50 at 60% w/w solids in ethanol. This RAFT solution homopolymerisation was monitored by $^1$H

TABLE 2

Conversions, molecular weights ($M_n$), polydispersities ($M_w/M_n$), and morphologies obtained for Poly(NMEP)₅₀-poly(BzMA)$_x$ (denoted as N₅₀—B$_x$ for brevity) diblock copolymer nanoparticles prepared at various solids content.

| Example | Diblock Composition | Conversion$^a$ (%) | Solids Content (% w/w) | GPC$^b$ $M_n$ (kg/mol$^{-1}$) | $M_w/M_n$ | Morphology |
|---|---|---|---|---|---|---|
| 17 | N₅₀—B₆₉ | 93 | 20 | 13.1 | 1.20 | Spheres$^c$ |
| 18 | N₅₀—B₉₃ | 93 | 20 | 14.4 | 1.21 | Spheres$^c$ (with short worms) |
| 19 | N₅₀—B₁₁₅ | 94 | 20 | 16.4 | 1.21 | Worms$^d$ |
| 20 | N₅₀—B₁₄₄ | 96 | 20 | 17.9 | 1.24 | Worms$^d$ |
| 21 | N₅₀—B₁₅₈ | 90 | 20 | 19.7 | 1.20 | Worms$^d$ (with vesicles) |
| 22 | N₅₀—B₁₈₈ | 94 | 20 | 21.2 | 1.23 | Vesicles$^c$ |
| 23 | N₅₀—B₂₃₃ | 93 | 20 | 24.1 | 1.25 | Vesicles$^c$ |

$^a$Monomer conversion determined by $^1$H NMR spectroscopy in CDCl₃
$^b$Determined by DMF GPC against PMMA calibration standards
$^c$Determined by TEM
$^d$Determined by SEM NMR spectroscopy. Very high conversion (97%) was achieved after 6 h. This unpurified Poly(NMEP) macro-CTA was then chain-extended with BzMA at 70° C., targeting a Poly(BzMA) DP of 250 at 30% w/w solids. A final comonomer conversion of 97% was achieved after 24 h. Spherical micelles with a mean diameter of 21±2 nm were observed after just 1 h, but these transformed to worm-like micelles after 2 h and then to vesicles after 8 h. The final morphology after 24 h was vesicles. A linear increase in $M_n$ with conversion and a low final dispersity ($M_w/M_n$=1.15) were observed for the synthesis of the Poly(NMEP)$_{47}$ macro-CTA via RAFT solution polymerization. The subsequent RAFT dispersion polymerisation of BzMA also resulted in a linear evolution in molecular weight (and a modest increase in dispersity) with conversion. The final Poly(NMEP)$_{47}$-poly(BzMA)$_{243}$ diblock copolymer had an $M_n$ of 23.6 kg mol$^{-1}$ and a dispersity of 1.21.

Pickering Emulsions

Example 25

A 10 g batch of 25 nanometer diameter Poly(SMA)$_{14}$-poly(NMEP)$_{49}$ spheres was prepared at 10% w/w solids in n-dodecane. Homogenization of n-dodecane nanoparticle dispersions with water resulted in water-in-oil and oil-in-water Pickering emulsions. The emulsions were analyzed by optical microscopy and laser diffraction techniques.

Characterization of Copolymers and Pickering Emulsions $^1$H NMR Spectroscopy.

All $^1$H NMR spectra were recorded at 20° C. in either $CD_2Cl_2$ or $CDCl_3$ using a 400 MHz Bruker. Avance-400 spectrometer with 64 scans were averaged per spectrum.

GPC analysis of Poly(SMA)-poly(NMEP) and Poly(NMEP)-poly(BzMA) diblock copolymers:

The molecular weights and polydispersities of Poly(SMA)-poly(NMEP) diblock copolymers were obtained using a GPC set-up comprising a Hewlett Packard HP1090 Liquid Chromatograph pump unit and two Polymer Laboratories PL gel 5 μm 'Mixed C' columns connected in series with a guard column at 40° C. connected to a Gilson Model 131 refractive index detector. The eluent was a 3:1 v/v % chloroform/methanol mixture containing 2 mM LiBr at a flow rate of 1.0 ml per minute. A series of near-monodisperse PMMA standards were used for calibration. Data analysis was carried out using Cirrus GPC software supplied by Agilent.

The molecular weights and dispersities of Poly(NMEP)-poly(BzMA) diblock copolymers were determined by DMF GPC at 60° C. The GPC set-up consisted of two Polymer Laboratories PL gel 5 μm 'Mixed C' columns connected in series to a Varian 390 LC multidetector suite (refractive index detector) and a Varian 290 LC pump injection module. The mobile phase was HPLC-grade DMF containing 10 mmol LiBr and flow rate was 1.0 ml min$^{-1}$. A series of ten near-monodisperse PMMA samples were used as calibration standards and DMSO was used as a flow rate marker. Data were analyzed using Varian Cirrus GPC software (version 3.3).

DLS.

The intensity-average hydrodynamic diameter of each batch of nanoparticles was determined at 25° C. using a Malvern Zetasizer NanoZS instrument at a scattering angle of 173°. Dilute Poly(SMA)-poly(NMEP) diblock copolymer dispersions (0.20% w/w) in n-heptane were analysed using quartz cuvettes and data was averaged over three consecutive runs. Dilute Poly(NMEP)-poly(BzMA) diblock copolymer dispersions (0.20% w/w) in ethanol were analyzed using disposable plastic cuvettes. The data was averaged over three consecutive runs.

TEM analysis of Poly(SMA)-poly(NMEP) and Poly(NMEP)-poly(BzMA) diblock copolymers:

Copper/palladium TEM grids (Agar Scientific, UK) were coated in-house to yield a thin film of amorphous carbon. Dilute dispersions of Poly(SMA)-poly(NMEP) diblock copolymers (0.20% w/w in n-heptane, 10.0 μL) were placed on the carbon-coated grids and left for 30 min to allow solvent evaporation. The grids were exposed to ruthenium (VIII) oxide vapour for 7 min at 20° C. prior to analysis.

The poly(NMEP)-poly(BzMA) grids were subjected to a glow discharge for 30 seconds to create a hydrophilic surface. Individual samples (0.20% w/w dispersion in ethanol, 10.0 μL) were adsorbed onto the freshly treated grids for one minute and then blotted with filter paper to remove excess solution. To stain the colloidal aggregates, uranyl formate (9.0 μL of a 0.75% w/w solution) was absorbed onto the sample-loaded grid for 20 seconds and then carefully blotted to remove excess stain. The grids were then dried using a vacuum hose.

Both sets of grids were imaged using a Philips CM100 instrument operating at 100 kV and equipped with a Gatan 1 k CCD camera.

SEM.

Samples were analysed using a FEI Inspect F scanning electron microscope at 10 kV. All samples were gold-coated for about 60 seconds using a current of 15 mA prior to imaging to prevent sample charging.

Optical Microscopy.

Optical microscopy images of emulsion droplets were recorded using a Motic DMBA300 digital biological microscope equipped with a built-in camera and Motic Images Plus 2.0 ML software.

Laser Diffraction.

Emulsions were sized using a Malvern Mastersizer 2000 instrument equipped with a small volume Hydro 2000SM sample dispersion unit (ca. 50 ml), a HeNe laser operating at 633 nm, and a solid-state blue laser operating at 466 nm. The stirring rate was adjusted to 1000 rpm in order to avoid creaming of the emulsion during analysis. After each measurement, the cell was rinsed once with ethanol, followed by two rinses with distilled water; the glass walls of the cell are carefully wiped with tissue to avoid cross-contamination and the laser was aligned centrally to the detector prior to data acquisition.

DLS analysis of the Poly(SMA)$_{14}$-Poly(NMEP)$_x$ diblock copolymer nanoparticles indicated a monotonic increase in the intensity-average diameter when targeting higher Poly(NMEP) DPs. DLS size distributions were relatively narrow in all cases: the smallest nanoparticles (Poly(SMA)$_{14}$-Poly(NMEP)$_{49}$) were only 23 nm in diameter, while the largest nanoparticles (Poly(SMA)$_{14}$-Poly(NMEP)$_{960}$) had a diameter of 462 nm.

TEM studies of series of Poly(SMA)$_{14}$-Poly(NMEP)$_x$ diblock copolymer nanoparticles prepared at 10% w/w solids indicated an exclusively spherical morphology. The Poly(SMA)$_{14}$-Poly(NMEP)$_{19}$s composition is particularly interesting, since varying the copolymer concentration yields the full range of morphologies (spheres, worms and vesicles). Thus a near-monodisperse spherical morphology was observed at 10% w/w solids, whereas worms (approximate worm width=100 nm, but highly polydisperse in worm contour length) were produced at 20% w/w solids and a vesicle phase comprising mainly oligolamellar vesicles was formed at 30% w/w solids.

What we claim is:

1. A block copolymer comprising:
   (a) at least one block A consisting of repeating units derived from at least one monomer $a_1$ and
   (b) at least one block B comprising repeating units derived from at least one hydrophobic monomer $b_1$ and optionally, at least one monomer $a_2$ with the proviso that said monomer $b_1$ is not lauryl(meth)acrylate;
   wherein each said monomer $a_1$ and $a_2$ independently has a structure:

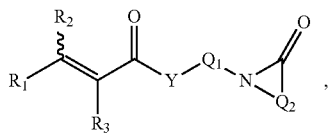

wherein
Y is oxygen, $NR_7$ or sulfur;
$R_7$ is selected from the group consisting of hydrogen, functionalized and unfunctionalized alkyl, and combinations thereof;
each $Q_1$, and $Q_2$, is independently a functionalized or unfunctionalized alkylene; and
each said $R_1$ and $R_3$ is independently hydrogen or methyl;
said $R_2$ is

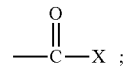

X is selected from the group consisting of $OR_4$, OM, halogens, and $N(R_5)(R_6)$; each $R_4$, $R_5$, and $R_6$ is independently selected from the group consisting of hydrogen and functionalized and unfunctionalized alkyl; and each M is independently selected from the group consisting of metal ions, ammonium ions, organic ammonium-cations, and combinations thereof.

* * * * *